(12) United States Patent
Meyer et al.

(10) Patent No.: US 6,496,561 B1
(45) Date of Patent: Dec. 17, 2002

(54) DEVICES, METHODS AND SYSTEMS FOR DELIVERY OF X-RAY

(75) Inventors: Steven Thomas Meyer, St. Paul, MN (US); Victor Ivan Chornenky, Minnetonka, MN (US); Patrick D. Andre, Minneapolis, MN (US); Thomas E. Eibs, St. Louis Park, MN (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 09/036,602

(22) Filed: Mar. 6, 1998

(51) Int. Cl.[7] .................................................. A61N 5/10
(52) U.S. Cl. .......................................... 378/65; 604/21
(58) Field of Search ................................ 378/65; 604/21

(56) References Cited

U.S. PATENT DOCUMENTS

| | | |
|---|---|---|
| 4,762,129 A | 8/1988 | Bonzel |
| 5,002,531 A | 3/1991 | Bonzel |
| 5,040,548 A | 8/1991 | Yock |
| 5,061,273 A | 10/1991 | Yock |
| 5,103,395 A | 4/1992 | Spako et al. |
| 5,232,445 A | 8/1993 | Bonzel |
| 5,247,555 A | 9/1993 | Moore et al. |
| 5,361,768 A | 11/1994 | Webler et al. |
| 5,485,846 A | 1/1996 | Webler et al. |
| 5,592,942 A | 1/1997 | Webler et al. |
| 5,620,438 A | 4/1997 | Amplatz et al. |
| 5,643,171 A | 7/1997 | Bradshaw et al. |
| 5,653,683 A | 8/1997 | D'Andrea |
| 5,741,246 A | 4/1998 | Prescott |
| 5,748,699 A * | 5/1998 | Smith .......................... 378/65 |

FOREIGN PATENT DOCUMENTS

| | | | |
|---|---|---|---|
| EP | 0 546 221 | 6/1993 | |
| EP | 0 564 894 | 10/1993 | |
| EP | 0 832 670 | 4/1998 | |
| WO | WO 93/20882 | 10/1993 | |
| WO | WO 94/02194 | 2/1994 | |
| WO | WO97/07740 | * 3/1997 | .................. 378/65 |

OTHER PUBLICATIONS

Chornenky, V., "The Soft X–Ray System" (Ch. 14), *Handbook of Vascular Brachytherapy*, Waksman et al., Eds., Martin Dunitz, Ltd., London, Mar. 1998 (6 pages).

* cited by examiner

*Primary Examiner*—Craig E. Church

(57) ABSTRACT

The present invention includes a device for X-ray treatment in a passage, a method for positioning an X-ray emitter at a treatment area in the passage, a method for exposing a length of the treatment area, and a method for moving a catheter automatically. In addition, the present invention includes a bellows valve adapter and a hemostasis valve adapter that allows fluid to circulate between a sheath and an X-ray emitter within the device and allows movement of the X-ray emitter within the sheath. Further, the invention includes a catheter pullback assembly for retracting or advancing an X-ray emitter, a system for X-ray treatment in a body, and a treatment system for controlling an X-ray emitter.

54 Claims, 13 Drawing Sheets

DEVICES, METHODS AND SYSTEMS FOR DELIVERY OF X-RAY

FIELD OF THE INVENTION

The present invention is directed to devices, methods and systems for administering localized radiation to vessels, lumens, or cavities of a body, such as cardiovascular tissue, to treat restenosis and other conditions.

BACKGROUND OF THE INVENTION

In the medical field, doctors and scientists strive to find less invasive ways to treat patients. By using treatments that are less intrusive to the body, doctors can greatly reduce the stress on the patient's systems and exposure to infection. For example, laparoscopic techniques enable physicians to explore the interior of the body and perform surgery through a small opening in the skin. Less intrusive medical techniques are extremely beneficial when applied to cardiovascular diseases.

Cardiovascular diseases affect millions of people, often causing heart attacks and death. One common aspect of many cardiovascular diseases is stenosis, or the thickening of the artery or vein, decreasing blood flow through the vessel. Angioplasty procedures have been developed to reopen clogged arteries without resorting to a bypass operation. However, in a large percentage of cases, arteries become occluded again after an angioplasty procedure. This recurrent thickening of the vessel is termed restenosis. Restenosis frequently requires a second angioplasty and eventual bypass surgery. Bypass surgery is very stressful on the patient, requiring the chest to be opened, and presents risks from infection, anesthesia, and heart failure.

Effective methods of preventing or treating restenosis could benefit millions of people. One treatment for restenosis that has been attempted is beta-irradiation of the vessel wall by positioning radioactive isotopes in the vessel at the site of the restenosis. However, the depth of the penetration of the radiation is difficult to control with this method. The depth of the radiation is determined by the type of the radio-isotope used. The radioactive source will also irradiate other healthy parts of the body as it is brought to the site to be treated. Another disadvantage is that medical personnel must take extensive precautions when handling storing, and disposing the radioactive material.

Less intrusive techniques are also extremely beneficial when applied to the esophagus. Tens of millions of Americans suffer from gastroesophageal reflux disease (GERD). GERD is characterized by a backward flow of the stomach and duodenal contents into the esophagus. These conditions result when the valve at the junction between the esophagus and the stomach does not function properly. When this occurs frequently, it is termed chronic GERD or reflux esophagitis. The symptoms of this condition are dyspepsia, or discomfort in the esophagus after meals, burning chest, upper abdominal pain, sour taste, and regurgitation.

Medical research has revealed that the acidic stomach contents cause anatomic abnormalities of the epithelium, or lining, of the esophagus during reflux. The cell type of the epithelium of the esophagus changes from a squamous, or circular-shaped cell, to a columnar, or rectangular-shaped, cell type. This cellular damage of the epithelium is termed Barrett's esophagus.

Barrett's esophagus is a precursor for cancer of the gastroesophageal system. Barrett's-associated malignancies strike approximately 10,000 people per year. There is a high rate of progression from reflux disease to Barrett's esophagus. In fact, 90 percent of patients with reflux symptoms who have an endoscopic examination show anatomic abnormalities of the epithelium.

Diagnosis of cancer in Barrett's esophagus ordinarily leads to removal of the diseased segment of the esophagus. However, an effective treatment of Barrett's disease could prevent the progression to cancer and could therefore reduce the need for this painful and drastic procedure. An effective treatment for Barrett's esophagus could improve the lives of many people. Ultrasound and argon-ion plasma treatments have been suggested to treat Barrett's esophagus, but these techniques are in early experimental stages and have not been proven effective. It is believed that photodynamic therapy is also a possibility.

Many other disorders could be treated with small, effective medical devices capable of accessing the interior of the body. For example, one disorder of the gastrointestinal system is pyloric strictures. Pyloric strictures occur in the pylorus, or distal aperture of the stomach. The pylorus is surrounded by a strong band of circular muscle, through which the stomach contents are emptied into the duodenum. Pyloric strictures can be subjected to dilatation to open the pylorus passage. However, the pylorus frequently thickens in response to the dilatation. Repeated dilatation has been used to treat pyloric strictures, but has not proven to be an effective long-term solution. There is a need for treatments to prevent this recurrent thickening of the pylorus.

Thus, there is a need for miniature devices and effective methods to treat the interior of the body with minimal intrusion. Effective, less invasive techniques for treating stenosis and restenosis of a lumen, treating GERD, and treating pyloric strictures are especially needed.

Recently, X-ray radiation has been realized to provide a very promising way to treat these types of conditions. Ionizing radiation penetrates to the first layers of cells on the surface of the passage or lumen. This radiation induces apoptosis, or programmed cell death.

Apoptosis differs from another type of cell death, necrosis. In apoptosis, a disruption in the gene structure of the cell results in the cell failing to replicate, and in some cells, results in an induced cell death where the contents of the cell are utilized by adjacent cells. Cell death by apoptosis therefore reduces inflammation and the biochemical results of inflammation, as compared to necrosis, which results in scarring and thickening of the surface cells.

X-ray device radiation of the esophagus may be used to treat Barrett's esophagus by inducing apoptosis in the abnormal cells of the epithelium. The escalation of this condition to cancer may be reduced. X-ray radiation can also be used for preventing the thickening of the pylorus after dilatation of pyloric strictures.

X-ray radiation has been found to reduce the occurrence of restenosis when X-ray radiation is applied to area of a blood vessel where an angioplasty or other expansion of the vessel has taken place. In coronary applications, it is desirable to have the X-ray radiation penetrate into the adventitia tissue. The advantages and disadvantages of X-ray radiation penetration into the cardiac muscle tissue are still being investigated. Further, it is desirable to deliver X-ray radiation with a peak energy of about 6–15 kiloelectron volts (keV) in coronary applications. The peak energy may also be 8–10 kiloelectron volts.

X-ray treatment devices for these types of applications must be small and flexible enough to fit inside the vessels and passages, yet have enough rigidity and structural integrity so that they can be advanced a distance through the body and contain the advanced treatment device. In the case where an X-ray device is to be delivered through vessels and passages, there is also the additional complication of providing a high voltage to the treatment device while inside the body. Using the X-ray device may generate heat inside the patient, and the delivery system should prevent any heat from damaging surrounding tissue. If the treatment area is large enough that it cannot be treated from one point inside the body, the treatment device may have to be moved across the treatment area during therapy.

Thus there is a need for delivery formats to be used for example in connection with an X-ray device for emitting localized radiation inside a patient's body. The delivery formats need to include devices and methods that deliver the treatment device reliably to the treatment site, treat the site uniformly and deliver a predictable dose, while being easy to use and avoiding invasive steps in the treatment.

SUMMARY OF THE INVENTION

The invention relates to a device for X-ray treatment in a passage of a body, a method for positioning an X-ray emitter in a passage of a body, a method for exposing a length of a treatment area to X-ray radiation and a method for automatically moving an X-ray catheter. Further, the invention relates to a valve adapter for allowing fluid flow under pressure to the interior of a sheath and allowing movement of the cable relative to the sheath. The invention further relates to a catheter pullback assembly and a treatment system.

A device suitable for X-ray treatment in a passage within a body of a patient is described, including a sheath that has a wall, a proximal end, and a distal end, where the sheath wall defines a primary lumen longitudinally through the sheath, and an X-ray emitter coupled to a cable, positionable within the primary lumen so that the X-ray emitter is near the distal end of the sheath.

The device may further include a stylet defining a stylet lumen, wherein the stylet is positionable within the primary lumen.

The sheath of the device may define a parking lumen adjacent to a portion of the primary lumen. The parking lumen has a proximal end and a distal end and the distal end of the parking lumen has an opening to the primary lumen and the proximal end of the parking lumen has an opening to the exterior of the sheath.

The sheath may alternatively define a parking lumen adjacent to a portion of the primary lumen, including openings to the exterior of the sheath. The X-ray emitter may be moveable within the primary lumen or fixed within the lumen near the distal end of the sheath.

The device may also include a guide wire segment coupled to the distal end of the sheath. The X-ray emitter may be movable within the primary lumen or fixed within the primary lumen near the distal end of the sheath.

The invention also provides a method for positioning an X-ray emitter at a treatment area in a passage within a body of a patient. The method includes the step of moving a guide wire, having a proximal end and a distal end, through the passage so that the distal end is distal to the treatment area, advancing a sheath over the proximal end of the guide wire, where the sheath has a proximal end, a distal end and a primary lumen extending longitudinally through the sheath and receiving the guide wire so that the distal end of the sheath is distal to the treatment site, withdrawing the guide wire from the primary lumen, and placing the X-ray emitter coupled to a cable in the primary lumen so that the X-ray emitter is positioned distal to the treatment site.

Also described is an alternative method for positioning an X-ray emitter at a treatment area in a passage within a body of a patient. The method includes moving a guide wire having a proximal end and a distal end, through the passage so that the distal end is distal to the treatment area, advancing the sheath, defining a parking lumen adjacent to a portion of the primary lumen and having a proximal end and a distal end, the distal end of the parking lumen having an opening to the primary lumen and the proximal end of the parking lumen having an opening to the exterior of the sheath, where the sheath is advanced by inserting the guide wire into the distal end of the primary lumen and into the parking lumen so that the distal end of the sheath is distal to the treatment area, and placing the X-ray emitter at the distal end of the sheath within the primary lumen.

Another method for positioning an X-ray emitter is described where the sheath defines a parking lumen adjacent to a portion of the primary lumen. The parking lumen has a proximal end and a distal end that have openings to the exterior of the sheath, the sheath being advanced so that a distal end of the sheath is distal to the treatment area by placing the guide wire into the parking lumen, and placing the X-ray emitter at the distal end of the sheath within the primary lumen.

An alternative method for positioning an X-ray emitter includes a guide wire segment extending beyond the distal end of the sheath, so that the distal end is distal to the treatment area.

The present invention also describes a method of exposing a length of treatment area in a patient to X-ray radiation, where the X-ray emitter is coupled to a connector at the distal end of the connector. The method includes providing a sliding carriage mounted on a body, the carriage being attached to a proximal end connector and attached to an actuator and controlling the actuator and connector to apply X-ray radiation across the length of the treatment area by moving the X-ray emitter.

The present invention also describes a method of moving a catheter inside a sheath automatically across a length of a treatment area, while the distal end of the catheter is positioned inside a patient. The method includes providing a pullback assembly having a body and a sliding carriage, where the carriage is attached to the proximal end of the cable support tube and to an actuator, and the body is attached to the proximal end of the sheath, and automatically controlling the actuator to move the carriage.

A bellows valve adapter for allowing fluid flow around an X-ray emitter and permitting positioning of the X-ray emitter is also part of the present invention. The adapter includes a catheter sheath having a distal and a proximal end, a cable support tube, having a distal and a proximal end, where the distal end of the support tube and a portion of the support tube are inside the catheter sheath, and a bellows being a collapsible tube having a first and a second end, where the first end of the bellows is connected to the proximal end of the catheter sheath and second end is connected to the proximal end of the cable support tube.

A hemostasis valve adapter for allowing fluid flow around an X-ray emitter and permitting positioning of the X-ray emitter is provided. The valve adapter includes a catheter sheath, a cable support tube, where the distal end of the support tube and a portion of the support tube are inside the catheter sheath, and a seal device on the proximal end of the catheter sheath for sealing between the catheter sheath and the cable support tube, where the cable support tube is movable through the seal.

A catheter pullback assembly for retracting or advancing an X-ray emitter coupled to a cable is provided. The cable and the X-ray emitter may be positionable inside a catheter sheath, and the cable and X-ray emitter are movable relative to the catheter sheath. The assembly includes a body, a carriage mounted on the body, where the carriage is slidable with respect to the body, a distal pullback adapter is attached to a proximal end of the catheter sheath, where the adapter is mounted on the body, and a proximal pullback adapter, attached onto the cable, where the pullback adapter is mounted on the carriage.

A system for X-ray treatment in a passage within a body of a patient is also provided. The system includes a sheath, a cable support tube, where the distal end of the support tube and a portion of the support tube are inside the sheath, and an X-ray emitter coupled to a cable. The system also includes means for allowing fluid flow around the X-ray emitter and permitting positioning of the X-ray emitter, a cable pullback assembly having a body, a carriage mounted on the body the carriage slidable with respect to the body, distal pullback adapter sealed onto a proximal end of the sheath, where the distal pullback adapter is mounted on the body, and a proximal pullback adapter, sealed onto the cable, where the proximal pullback adapter is mounted on the carriage.

A system for controlling an X-ray emitter to deliver X-ray radiation to a treatment area within a patient is also provided. The system includes a pullback assembly having a body, a sliding carriage mounted on the body, a pullback adapter for the catheter luge mounted on the body, and a pullback adapter for the cable support tube mounted on the carriage. The system also includes a catheter sheath attached onto the distal pullback adapter, and the X-ray catheter includes the X-ray emitter operatively coupled to a connector, where the X-ray catheter is positioned within the catheter sheath lumen, and a control unit coupled to the connector and to the carriage, being capable of applying voltage to the connector and comprising a power source, an actuator for the pullback assy and a central processor.

These and various other advantages and features of novelty which characterize the invention are pointed out with particularity in the claims annexed hereto and forming a part hereof. However, for a better understanding of the invention, and its advantages, and the objects obtained by its use reference should be made to the accompanying drawings and descriptive matter, which form a further part hereof, and in which there is illustrated and described preferred embodiments of the invention.

BRIEF DESCRIPTION OF THE DRAWINGS

The invention may be more completely understood by considering the detailed description of various embodiments of the invention which follows in connection with the accompanying drawings, in which.

DETAILED DESCRIPTION OF INVENTION

Figure 1:
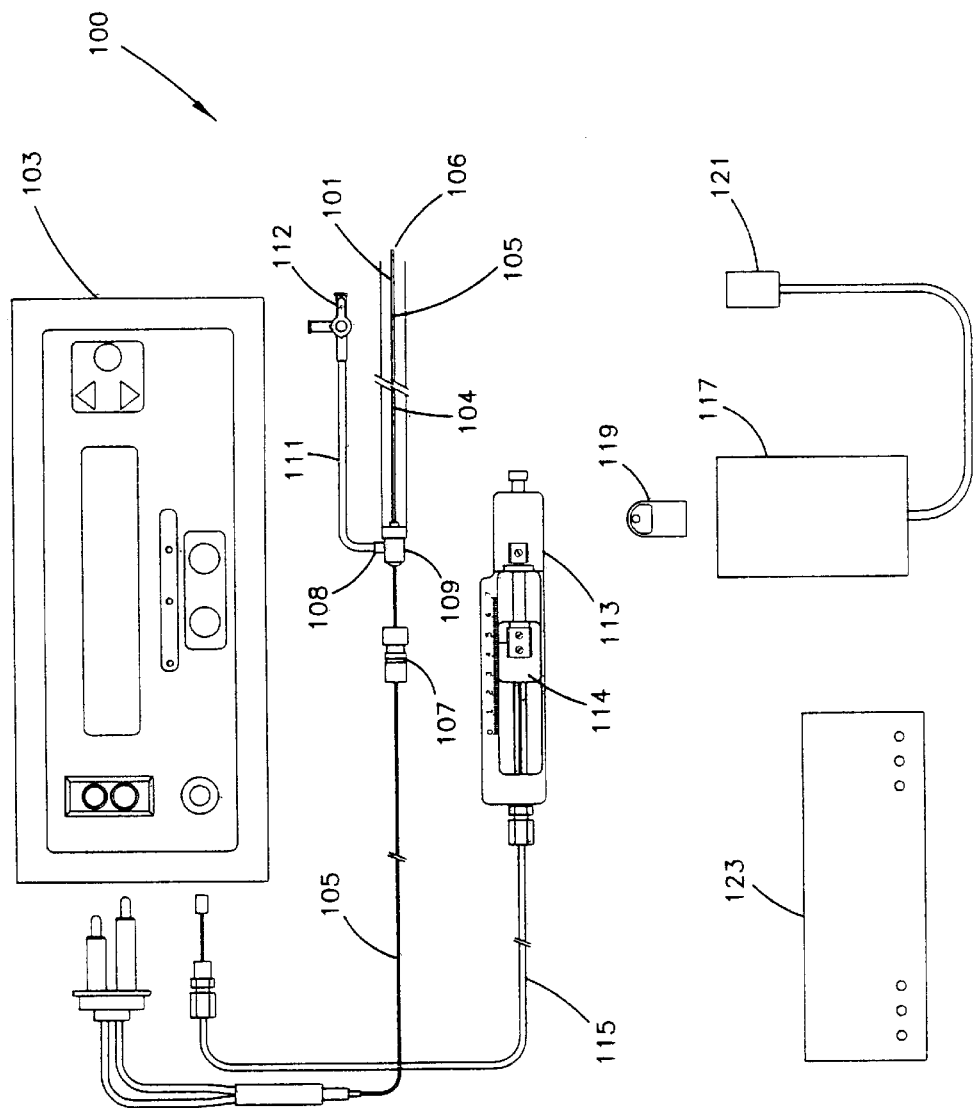
FIG. 1 is a schematic view of an embodiment of an X-ray treatment system in accordance with the invention.

The present invention includes a device for X-ray treatment in a passage, a method for positioning an X-ray emitter at a treatment area in the passage, a method for exposing a length of the treatment area to X-rays, and a method for moving a catheter automatically. In addition, the present invention includes a bellows valve adapter and a hemostasis valve adapter that allows fluid to circulate between a sheath and an X-ray emitter within the device and allows movement of the X-ray emitter within the sheath. Further, the invention includes a catheter pullback assembly for retracting or advancing an X-ray emitter, a system for X-ray treatment in a body, and a treatment system for controlling an X-ray emitter.

The device for X-ray treatment includes the sheath defining a primary lumen, and an X-ray emitter coupled to a cable. The device may include a parking lumen with a distal end which is connected to a distal most portion of the primary lumen. The parking lumen and the distal most portion of the lumen are fitted over the guide wire during the catheter tracking of the guide wire as is known in intravascular operations. In the alternative, the parking lumen may have openings to the exterior of the sheath at both the distal and proximal ends. In the devices with the parking lumen opening to the primary lumen, the guide wire can be retracted into the parking lumen after tracking, so that the primary lumen is available for the X-ray device without withdrawing the guide wire from the patient's body. In both types, the guide wire can be retracted into the parking lumen to prevent shadowing of X-rays. The device may alternatively have a guide wire segment coupled to the distal end of the sheath or to the X-ray emitter, that also leaves the primary lumen available for the X-ray device.

The device for X-ray treatment may alternatively include a sheath including a primary lumen and including a parking lumen for a guide wire that extends the length of the sheath.

The methods described for positioning the X-ray emitter may be used with the different devices for X-ray treatment of the invention. The method may include the steps of moving a guide wire through the passage so that the distal end of the guide wire is distal to the treatment area, advancing a sheath over the guide wire, withdrawing the guide wire from the primary lumen, and placing the X-ray emitter into the primary lumen so that the emitter is positioned at a distal end of the treatment area. The method for positioning may alternatively include advancing a sheath over a guide wire by placing the guide wire into a parking lumen of the sheath, and partially withdrawing the guide wire into the parking lumen so that the X-ray device may be introduced into the primary lumen without removing the guide wire from the body. One alternative method for positioning an X-ray emitter includes the steps of moving a sheath with a guide wire segment extending beyond the distal end through the passage, where it is not necessary to withdraw a guide wire.

The method of exposing a length of the treatment area utilizes sliding a carriage mounted on a pullback assembly, where the carriage is attached to the X-ray emitter via the cable. An actuator is used to move the carriage, and therefore move the X-ray emitter across the length of the treatment area. The method of moving the X-ray emitter inside a sheath automatically includes the step of automatically controlling the actuator to move the carriage.

The invention may also include a bellows valve adapter that comprises a catheter sheath, a cable support tube, and a bellows, where the first end of the bellows is connected to the proximal end of the catheter, and the second end is connected to the proximal end of the cable support tube. The hemostasis valve adapter includes a seal device that creates a seal between the catheter sheath and the cable support tube, and the cable support tube is movable through the seal.

The catheter pullback assembly for retracting or advancing the X-ray emitter is coupled to the cable and to the sheath so that the cable and X-ray emitter are movable relative to the catheter sheath. The system for X-ray treatment in a passage that is described permits fluid flow around the X-ray emitter, allows the X-ray emitter to be positioned at a distal end of the treatment area, and allows for movement of the emitter relative to the sheath. The system for controlling an X-ray emitter includes a control unit coupled to the connector and to the carriage of the pullback assembly.

The dosage of X-ray radiation to be applied to the interior of a body will generally be within the scope of the attending physicians judgment, and will be based on individual conditions, such as the condition of the site to be treated and the particular patient. For example, in order to treat the early stages Barrett's esophagus, only the first layer of cells may need to be irradiated. If Barrett's esophagus has progressed to a cancerous state, the amount of radiation delivered will typically increase.

According to the present invention, X-ray radiation in the range of 10 to 50 Grays may be applied to an area of the interior of a passage during treatment, for example, to prevent restenosis. Preferably, X-ray radiation in the range of 15 to 30 Grays may be applied to an interior body site. The treatment will be structured to last about 2 to 10 minutes, or, more preferably, 3 to 5 minutes. The X-ray emitter may be repositioned within the treatment area during the course of radiation treatment, depending on the length of the area requiring treatment. Step movements may be used, which are very simple to perform. In the alternative, the emitter may be moved continuously and slowly, which may result in more uniform treatment.

One embodiment of a treatment system according to the invention is shown in FIG. 1. The system may be used for delivering X-ray radiation to a treatment area inside a patient. The treatment area will typically be a short length of a body passage. For example, the interior surface of a length of a blood vessel or the esophagus may be a treatment site, that could benefit from local X-ray radiation.

The system includes the control unit 103, the catheter pullback assembly 113 and the X-ray catheter 101, part of which is shown. The X-ray catheter 101 includes a cable 105 and an X-ray emitter 106 having an anode and a cathode, that is capable of producing X-ray radiation when a high voltage is applied across the anode and cathode. The X-ray cable 105 supplies a high voltage to the X-ray catheter, for producing X-ray radiation. The X-ray catheter also includes a sheath 104. The X-ray catheter 101 is connected to the control unit 103 by the cable 105. The control unit 103 may control the voltage applied to the X-ray emitter, the movement of the X-ray emitter via an actuator, the saline flush of the catheter, the time length of radiation and many other treatment parameters. The control unit will be programmed by a health care professional with the correct dosage information. The catheter pullback assembly 113 has a sliding carriage 114 that is connected to the control unit 103 by the actuator cable 115. The actuator cable 115 may be actuated by the control unit 103 to move the carriage 114 of the catheter pullback assembly 113. The sliding carriage 114 will be attached to the cable 105, so that the actuator within the control unit 103 can be used to pull the emitter 106 across a treatment area. The sheath 104 is coupled to the stationary body of the pullback assembly 113, so that the actuator draws the X-ray emitter 106 back through the sheath 104.

Throughout the description, the term distal will be used to refer to the direction along the device toward the patient and toward the emitter, when the device is in use. The term proximal refers to the opposite direction.

The sheath 104 of the X-ray catheter 101 is connected to a distal pullback adapter 108, which is included on the pullback assembly 113. The distal pullback adapter 108 is used to secure the catheter sheath to the stationary body of the pullback assembly 113. The distal pullback adapter 108 may simply be a clip. A proximal pullback adapter 107 may be provided on the X-ray cable for moving the cable and the X-ray emitter inside the X-ray catheter 101. The distal pullback adapter may be a luer fitting, that is, a plastic fitting that can be secured or loosened around the cable that goes through the luer fitting. The distal pullback adapter 108 and proximal pullback adapter 107 may be mounted on the catheter pullback assembly for controlling the pulling back of the X-ray emitter. In the alternative, the proximal pullback adapter could be eliminated, and the carriage could be clipped directly to the cable 105.

A fluid supply tube or port 111 is connected to the distal pullback adapter 108. The fluid supply tube 111 and a fluid valve support 112 may, for example, be used to provide a flow of fluid, such as saline solution, around the cable and X-ray emitter inside the sheath, in order to carry away heat that may be generated by the X-ray emitter during operation. The distal pullback adapter 108 may include a hemostasis valve 109, that will be further described, that allows the cable to move relative to the sheath, but still provides a fluid seal around the cable.

Therapy parameters and operating parameters may be stored on a data key or similar memory device 119. The parameters are stored on the data key 119, for example, by inserting the data key 119 into the control unit 103. The data key 119 may be inserted into a data key reader 117. The data key reader 117 may download the parameter data to, for example a personal computer (not shown), via the serial port cable 121. These components may be used to store data about a particular patient's treatment history.

A battery charger 123 may be provided to recharge batteries used in the control unit 103. Many different battery chargers may be used with this embodiment. For example, a commercially available battery charger, such as one marketed by Patco Electronics under the model number 300-12 may be used with this embodiment. The battery charger may be supplied either as an external component or embedded within the control unit.

The X-ray device according to the invention comprises a sheath with a wall, the sheath having proximal and distal ends and a primary lumen longitudinally through it. The sheath may be formed from many different elastomeric materials that are suitable in consideration of the intended application of the embodiment. In one application, for example, the sheath is to be advanced through a blood vessel in a patient, to position the X-ray device in the vicinity of a treatment area. The sheath may for example be formed from a polymer material using well known extrusion techniques or other processing techniques. The sheath may be polyimide tubing, that is a chemically inert polymer. Polyimide tubing also has many other desirable qualities. Polyimide is thermally stable, and exhibits radiation, solvent and cryogenic resistance. One commercial source for polyimide tubing is HVT Technologies, in Treton, Ga.

The embodiments of the device according to the invention also feature an X-ray emitter coupled to a cable. The cable may supply voltage to the X-ray emitter for producing X-ray radiation, and may be used in positioning the X-ray emitter. Constructions and methods for use of the X-ray emitter and cable are described in co-pending patent application "X-ray Catheter", with Ser. No. 08/701,764, the contents of which are incorporated by reference herein.

An X-ray device of the present invention includes an anode and a cathode, arranged within a vacuum housing to produce X-ray radiation. The cathode may include a thin diamond film, and may include a getter material that is activated to improve the quality of the vacuum within the housing, as described in U.S. patent application Ser. No. 08/806,244 that is incorporated by reference herein. The vacuum housing may include a diamond shell, as described in the U.S. patent application Ser. No. 09/008,202 titled "HOUSING FOR MINIATURE X-RAY DEVICE", filed on Jan. 16, 1998, which is hereby incorporated by reference herein.

Options for the voltage source of the present invention are discussed in U.S. Provisional Patent Applications "METHOD AND X-RAY DEVICE USING PULSE HIGH VOLTAGE SOURCE", having Ser. No. 60/077,057 and "METHOD AND X-RAY DEVICE USING ADAPTABLE POWER SOURCE", having Ser. No. 60/077,058. Both applications were filed Mar. 6, 1998, and both applications are incorporated by reference in their entireties.

The X-ray catheter is introduced into a patient's body using ordinary techniques in the art. For example, where the X-ray catheter is to be introduced into a blood vessel, typically, an incision is made to the blood vessel and a vessel expander is introduced. The vessel expander provides a pathway lumen into the vessel through which other implements, such as the guide wire and the sheath, can be introduced.

A guide wire having a proximal end and a distal end may be included in the device of the present invention. The guide wire may be used in advancing the sheath to the passage at the treatment area within the patient. For example, the guide wire may be steered through a patient's blood vessels until its distal end reaches the vicinity of a treatment area. The sheath may then be tracked over the guide wire to the vicinity of the treatment area along the guide wire. The guide wire may be manufactured from a number of materials. For example, the distal end of the guide wire may comprise a tightly wound coil of a metallic material, making it steerable through vessels in the patient's body.

The sheath may comprise a radiopaque marker on its distal end, for tracking the catheter while inside the patient's body. For example, fluoroscopy may be used as the visualization method. The emitter, if not radiopaque in itself, may also be provided with a radiopaque marker for tracking the X-ray emitter inside the patient's body.

Figure 2:
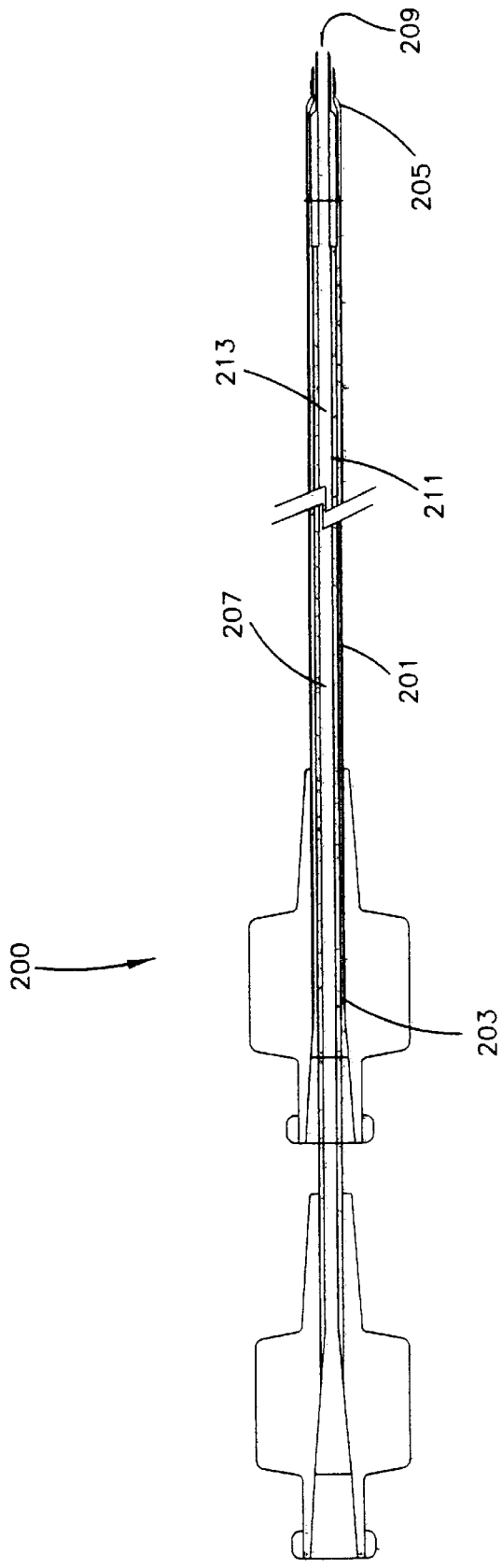
FIG. 2 is a schematic side view in cross-section of a first embodiment of an X-ray treatment device in accordance with the invention.

A first embodiment of a device suitable for X-ray treatment in a passage within a body of a patient is shown FIG. 2. The device 200 includes a sheath 201 comprising a wall, a proximal end 203, and a distal end 205. The sheath wall defines a primary lumen 207 longitudinally through the sheath. The sheath 201 further defines a distal opening 209 at the distal end 205. The device 200 may further comprise a removable stylet 211 defining a stylet lumen 213. The stylet may be used optionally to provide an increased stiffness to the device 200 during introduction of the catheter into the body. The material and configuration of the stylet may be chosen accordingly. For example, the stylet 211 may be formed from the same material as the sheath 201 with a greater thickness. Another alternative is to form the stylet 211 from a material with greater stiffness than that of the sheath 201.

In using the first embodiment of the device, a guide wire is moved through the passage within the patient's body so that a distal end of the guide wire is distal to the treatment area. A sheath 201 is then advanced over a proximal end of the guide wire. This may be done, for example, by inserting the proximal end of the guide wire into the distal opening 209 of the sheath 201 and the distal opening of the stylet 211 and advancing the sheath over the guide wire until the distal end of the sheath is distal to the treatment area. The guide wire is then withdrawn from the stylet lumen 213 while the sheath essentially remains stationary within the passage inside the patient. The stylet 211 if used, is then removed from the sheath 201. The advantage of using the stylet 211 is that it may provide the necessary stiffness to the sheath 201 when desirable during tracking over the guide wire, and that it may be removed before the X-ray emitter is introduced in the sheath 201, so as to provide the X-ray emitter with the maximum space available, and to avoid shadowing the X-ray radiation unnecessarily. An X-ray emitter coupled to a cable is then placed in the proximal end of the primary lumen so that the X-ray emitter is positioned at a distal end of the treatment area.

Figure 3:
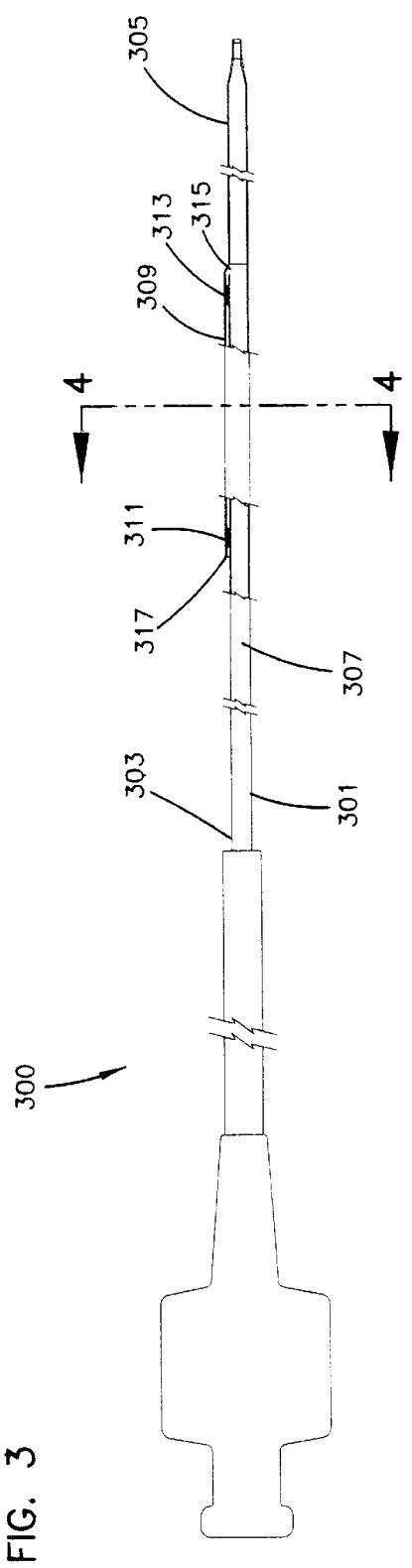
FIG. 3 is a schematic side view in cross-section of a second embodiment of an X-ray treatment device in accordance with the invention.

A second embodiment of the device according to the invention is shown in FIG. 3. The device 300 includes a sheath 301 with a proximal end 303 and a distal end 305. A wall of the sheath 301 defines a primary lumen 307 longitudinally through the sheath 301. The sheath 301 further defines a parking lumen 309 adjacent to a portion of the primary lumen 301. The parking lumen 309 has a proximal end 311 and a distal end 313. The distal end 313 has an opening 315 to the primary lumen 307. The proximal end 311 of the parking lumen 309 has an opening 317 to the exterior of the sheath 301.

Figure 4:
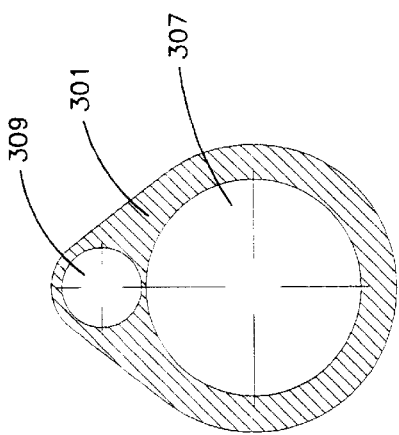
FIG. 4 is a front view in cross-section of the catheter sheath of FIG. 3 in accordance with the invention.

A cross-section of the second embodiment of the device according to the invention taken through the parking lumen 309 and primary lumen 307 is shown in FIG. 4. The sheath 301 has the parking lumen 309 adjacent the primary lumen 307. The sheath 301 can be formed in several different ways using well-known techniques. For example, sheath 301 may be formed by thermally adhering a tube comprising the parking lumen 309 to another tube comprising the primary lumen 307. The sheath 301 may also be formed, for example, by multi-lumen extrusion of a sheath comprising the parking lumen 309 and the primary lumen 307.

In using the second embodiment of the device, a guide wire is moved through the passage in the patient's body so that a distal end of the guide wire is distal to the treatment area. The sheath 301 is then advanced by inserting the proximal end of the guide wire into the distal end 305 of the sheath 301 and into the parking lumen 309 through the opening 315 until the distal end 305 is distal to the treatment area. The proximal end of the guide wire and a part of the guide wire will typically exit the parking lumen 309 through the opening 317. The sheath is tracked over a distal portion of the guide wire only: a distal-most portion of primary lumen and a second most distal portion at the parking lumen.

The guide wire is then partially withdrawn until the distal end of the guide wire is situated inside the parking lumen 309. The withdrawal of the guide wire into the parking lumen allows space for introducing the X-ray emitter into the primary lumen. Withdrawal of the guide wire also prevents the material of the guide wire from shadowing the radiation from the X-ray emitter during treatment. Once the guide wire is retracted, the X-ray emitter is placed at the distal end 305 of the sheath 301 within the primary lumen 307. This may, for example, be performed by inserting the emitter connected to a cable at a proximal end 303 of the sheath 301, and advancing the emitter through the primary lumen 307 to a position near the distal end 305 of the sheath 301.

The X-ray emitter may then be used for treatment by applying voltage across the anode and the cathode, and moving the X-ray emitter past the treatment area. Optionally, the cable may be connected to the pullback assembly as described below for uniform treatment.

Because of the placement of openings 315 and 317, the guide wire does not need to be fully withdrawn from the patient to allow for the introduction of the X-ray emitter into the primary lumen. A portion of the sheath, the parking lumen, remains tracked over the guide wire. If additional treatment in the body is desired, the emitter may be retracted distal to the parking lumen's distal end 315. The guide wire may be advanced further into the body of the patient, whereby the guide wire enters the primary lumen 307 from the parking lumen 309 through the opening 315. The guide wire then exits the primary lumen 307 at the distal end 305 of the sheath 301 into the parking lumen. Then the sheath may be advanced again until the distal end 305 is distal to the new treatment area, and a new treatment can be performed.

Alternatively, the guide wire and the sheath 301 may be withdrawn from the patient's body after the first treatment. The sheath 301 and the guide wire may be also be repositioned for a new treatment. Alternatively, though not desirably, the guide wire may be first be fully withdrawn from the patient's body, and the catheter may be withdrawn to one or more subsequent treatment areas.

Figure 5:
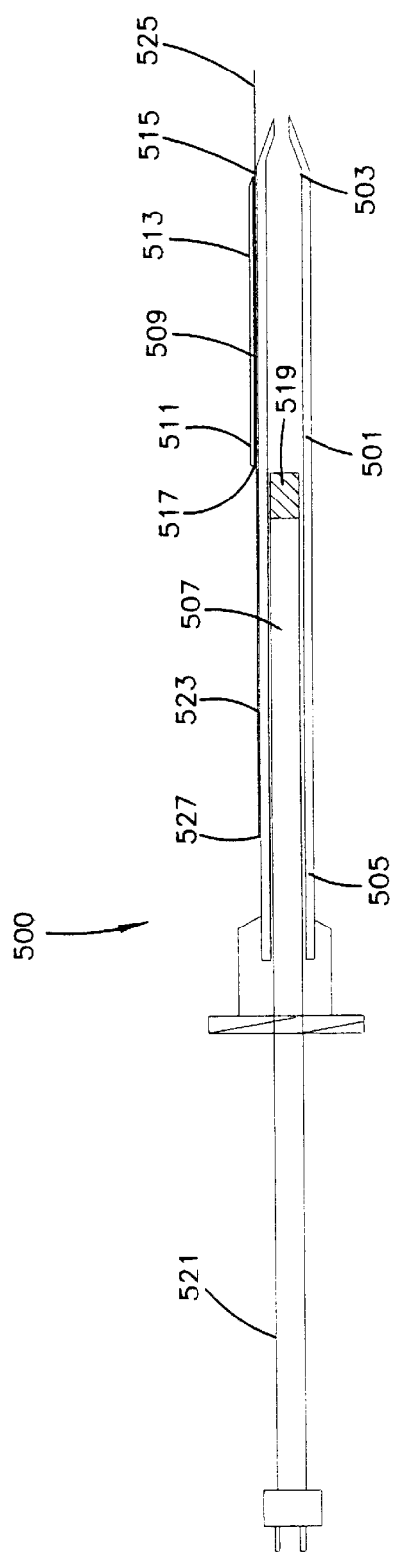
FIG. 5 is a schematic side view in cross-section of a third embodiment of an X-ray treatment device in accordance with the invention during tracking.
Figure 6:
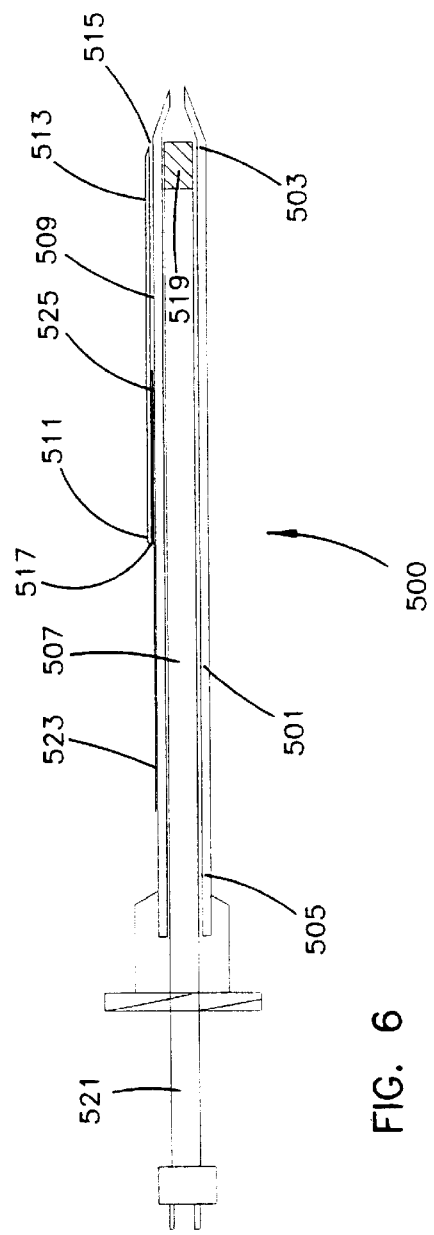
FIG. 6 is a schematic side view in cross-section of the third embodiment of an X-ray treatment device in accordance with the invention during treatment.

A third embodiment of the device according to the invention is shown in FIGS. 5 and 6. The device 500 includes a sheath 501 comprising a proximal end 505 and a distal end 503. A wall of the sheath defines a primary lumen 507 longitudinally through the sheath 501. The sheath 501 defines a parking lumen 509 adjacent to a portion of the primary lumen 507.

The sheath 501 can be formed in several different ways using well-known techniques. For example, sheath 501 may be formed by thermally adhering a tube comprising the parking lumen 509 to another tube comprising the primary lumen 507. The sheath 501 may also be formed, for example, by multi-lumen extrusion of a sheath comprising the parking lumen 509 and the primary lumen 507.

The parking lumen 509 has a proximal end 511 and a distal end 513. The proximal end 511 has an opening 517 to the exterior of the sheath 501. The distal end 513 also has an opening 515 to the exterior of the sheath 501. A guide wire 523 is shown adjacent to the sheath 501. With this configuration, it is possible to track the sheath over the guide wire without occupying the primary lumen. A portion of the guide wire 523 is inside the parking lumen 509. A distal end 525 of the guide wire 523 is shown distal to the sheath 501. An X-ray emitter 519 is shown in the primary lumen 507. The X-ray emitter 519 is connected to a cable 521, for advancing or withdrawing the emitter 519 in the primary lumen 507, and for supplying high voltage to the X-ray emitter 519.

In using the third embodiment, the guide wire 523 may be moved through the passage inside the patent's body so that the distal end 525 of the guide wire 523 is distal to a treatment area. The sheath 501 is then advanced so that a distal end 503 of the sheath 501 is distal to the treatment area. This may be performed by inserting a proximal end 527 of the guide wire 523 into the distal opening 515 of the parking lumen 509, and advancing the sheath 501 along the guide wire 523 until the distal end 503 is distal to the treatment area. The guide wire 523 may then be partially withdrawn until the distal end 525 is situated within the parking lumen 509. The X-ray emitter 519 may then be placed at the distal end 503, for example, by pushing the cable 521 into the primary lumen from outside the patient's body. The third embodiment of the device is shown in FIG. 6 as it would appear during treatment. The X-ray emitter 519 is situated at the distal end 503 of the sheath 501. The guide wire 523 has been withdrawn until the distal end 525 is within the parking lumen 509. Partial withdrawal of the guide wire 523 into the parking lumen may take place to prevent the material of the guide wire 523 from shadowing the radiation from the X-ray emitter 519.

The operator may place the X-ray emitter 519 in the primary lumen 507 before advancing the sheath 501 so that the distal end 503 of the sheath is distal to the treatment area. Alternatively the operator may advance the sheath 501 so that the distal end 503 is distal to the treatment area before placing the X-ray emitter 519 into the primary lumen 507.

After using the X-ray emitter, the guide wire 523 and the sheath 501 may be withdrawn from the patient's body. If further treatment is desired, the sheath 501 and the guide wire 523 may be withdrawn to a position for a new treatment. Alternatively, the guide wire 523 may be fully withdrawn from the patient's body, and the catheter may be withdrawn successfully to several subsequent treatment areas or other devices could be advanced through the primary lumen. Instead of withdrawing the guide wire 523, the operator also has the alternative of advancing the guide wire 523 further into the body of the patient. The guide wire then exits the parking lumen 509 through opening 515. The guide wire 523 may be advanced until the distal end 525 of the guide wire 523 is distal to a new treatment area, and the sheath 501 may be advanced until the distal end 503 is distal to the new treatment area. A new treatment can then be performed.

Figure 7:
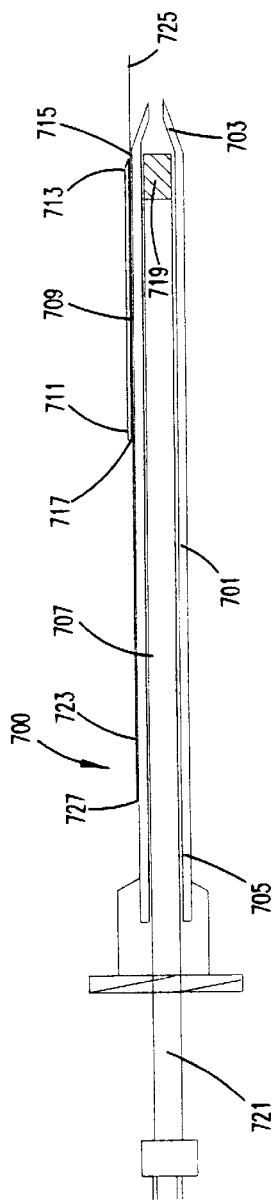
FIG. 7 is a schematic side view in cross-section of a fourth embodiment of an X-ray treatment device in accordance with the invention during tracking.
Figure 8:
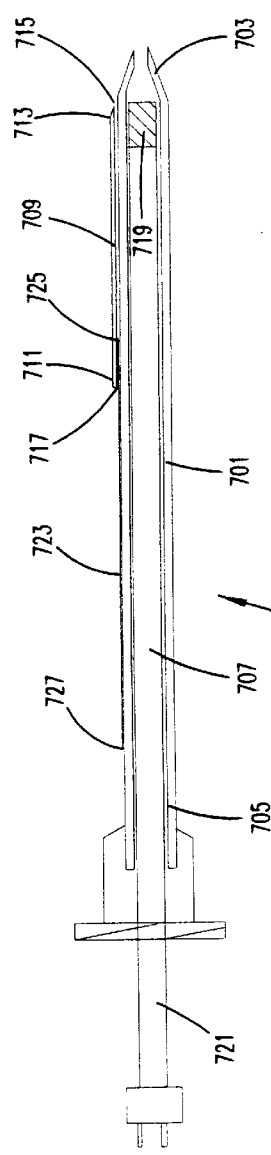
FIG. 8 is a schematic side view in cross-section of the fourth embodiment of an X-ray treatment device in accordance with the invention during treatment.
Figure 9:
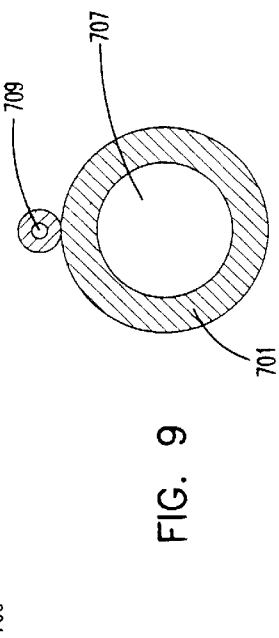
FIG. 9 is a schematic front view in cross-section of the catheter sheath of the fourth embodiment of an X-ray treatment device in accordance with the invention.

A fourth embodiment of the device according to the invention is shown during tracking in FIG. 7 and during treatment in FIG. 8. The device 700 includes a sheath 701 with a distal end 703 and a proximal end 705. A wall of the sheath 701 defines a primary lumen 707 longitudinally through the sheath 701. The sheath defines a parking lumen 709 adjacent to a portion of the primary 707. The parking lumen 709 has a proximal end 711 and a distal end 713. The proximal end 711 has an opening 717 to the exterior of the sheath 701. The distal end 713 has an opening 715 to the exterior of the sheath 701. A cross-section of the fourth embodiment of the device is shown in FIG. 9, as the sheath may appear if two polymer tubes were bonded together to form the sheath. The parking lumen 709 is shown adjacent to the primary lumen 707 of the sheath 701. The sheath 701 may be formed by several different well known techniques. For example, a tube comprising the parking lumen 709 may be thermally adhered to a tube comprising the primary lumen 707. Another example is multi-lumen extrusion of a sheath comprising the parking lumen 709 and the primary lumen 707. An X-ray emitter 719 is fixed within the primary lumen 707 near the distal end 703 of the sheath 701. The X-ray emitter 719 may be connected to a cable 721, for example, for supplying high voltage to the X-ray emitter 719. A guide wire 723 is shown in the parking lumen 709. A distal end 725 of the guide wire 723 is shown distal to the distal end 703 of the sheath 701.

In using the fourth embodiment, the guide wire is moved through the passage in the patient's body so that a distal end 725 is distal to the treatment area. The sheath 701 is advanced so that the distal end 703 is distal to the treatment area. This may, for example, be performed by inserting a proximal end 727 of the guide wire 723 into the opening 715 of the parking lumen 709, and advancing the sheath 701 along the guide wire until the distal end 703 is distal to the treatment area. The guide wire 723 is then partially withdrawn until the distal end 725 is situated inside the parking lumen 709. This configuration of the fourth embodiment is shown in FIG. 8. Withdrawal of the guide wire 723 may take place to prevent the material of the guide wire 723 from shadowing the radiation from the X-ray emitter 719.

After using the X-ray emitter, as previously described, the guide wire 723 and the sheath 701 may be withdrawn from the patient's body. If further treatment is desired, the sheath 701 and the guide wire 723 may be repositioned for a new treatment. Alternatively, the guide wire 723 may be first be fully withdrawn from the patient's body, and the catheter may be withdrawn successfully to several subsequent treatment areas. Instead of withdrawing the guide wire 723, the operator also has the alternative of advancing the guide wire 723 further into the body of the patient, whereby the guide wire 723 exits the parking lumen 709 through the opening 715. The guide wire 723 may be advanced until the distal end 725 is distal to a new treatment area, and the sheath 701 may be advanced until the distal end 703 is distal to the new treatment area, where a new treatment can be performed.

Figure 10:
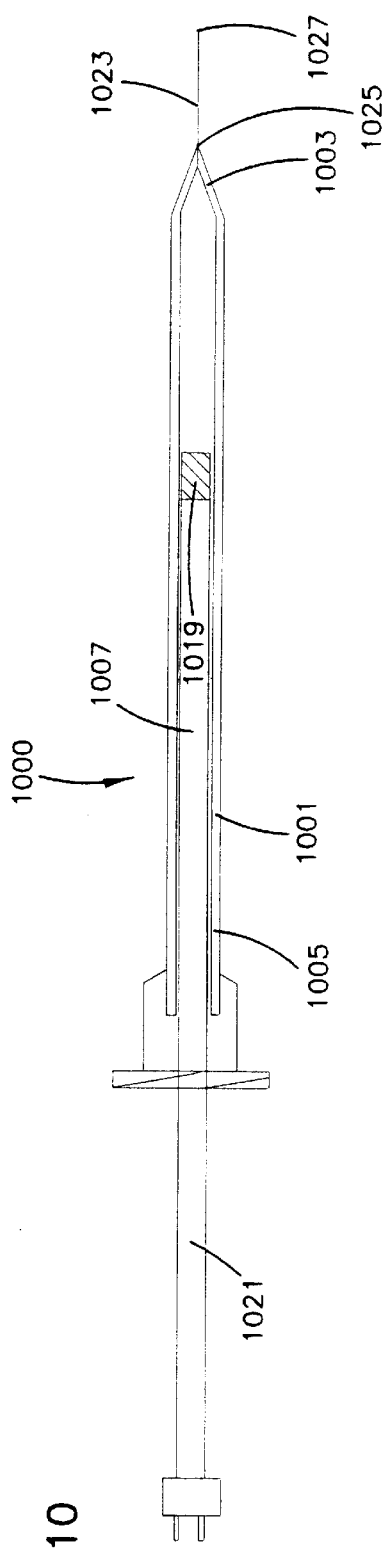
FIG. 10 is a schematic side view in cross-section of a fifth embodiment of an X-ray treatment device in accordance with the invention during tracking.
Figure 11:
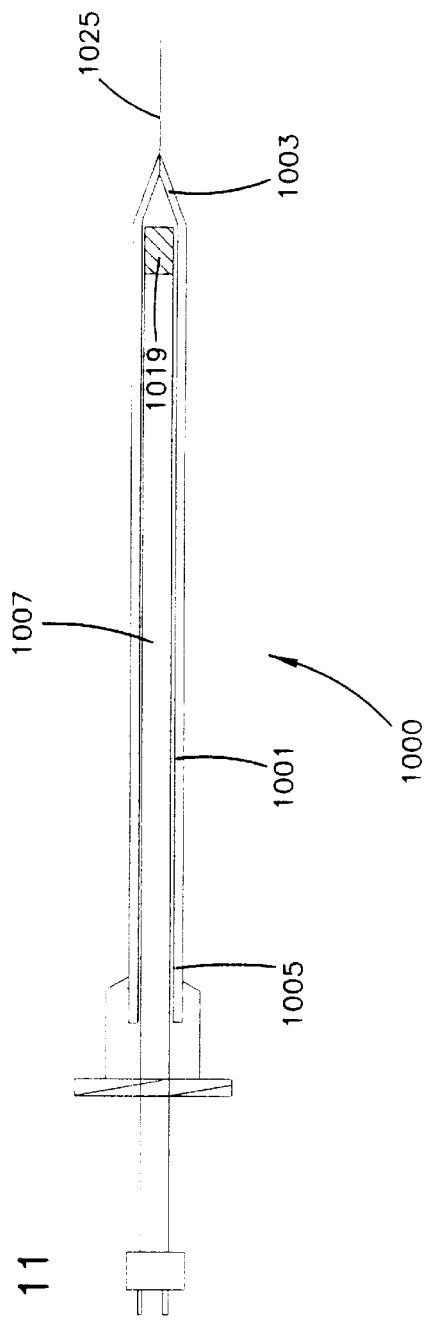
FIG. 11 is a schematic side view in cross-section of the fifth embodiment of an X-ray treatment device in accordance with the invention during treatment.

A fifth embodiment of the device according to the invention is shown in FIG. 10 during tracking and in FIG. 11 during treatment. The device 1000 includes a sheath 1001 having a distal end 1003 and a proximal end 1005. A wall of the sheath 1001 defines a primary lumen 1007 longitudinally through the sheath 1001. A guide wire segment 1023 having a proximal end 1025 and a distal end 1027 is coupled to the sheath. The guide wire segment 1023 coupled to the sheath does not take up space inside the primary lumen 1007 and does not shadow the radiation from the X-ray emitter 1019.

The proximal end 1025 of the guide wire segment 1023 is coupled to the distal end 1003 of the sheath 1001. Alternatively, the guide wire segment 1023 may be attached to the emitter 1019, such that the segment 1023 extends out the distal end 1023. An X-ray emitter 1019 is coupled to a cable 1021. The X-ray emitter 1019 is positionable within the primary lumen 1007 so that the X-ray emitter 1019 is near the distal end 1003 of the sheath 1001. The guide wire 1023 may be formed from different materials and have different configurations known in the art. For example, the guide wire segment 1023 may comprise a tightly wound coil of a metallic material. The distal ends may have openings or holes to allow flushing of liquid through the primary lumen.

In using the fifth embodiment, the sheath 1001 is moved through the passage inside the patient's body, so that the distal end 1003 is distal to the treatment area. During this step, the guide wire segment 1023 may help in steering the sheath 1001 to a position in the passage where the distal end 1003 is at a distal end of the treatment area. The X-ray emitter 1019 is positioned in the primary lumen 1007 so that the X-ray emitter 1019 is distal to the treatment area. This may be performed, for example, by advancing the X-ray emitter 1019 through the primary lumen 1007 using the cable 1021. This configuration of the fifth embodiment is shown in FIG. 11, where the X-ray emitter 1019 is near the distal end 1003 of the sheath 1001.

The operator may place the X-ray emitter 1019 in the primary lumen 1007 before advancing the sheath 1001 so that the distal end 1003 is distal to the treatment area. Alternatively the operator may advance the sheath 1001 so that the distal end 1003 is distal to the treatment area before placing the X-ray emitter 1019 into the primary lumen 1007.

After using the X-ray emitter 1019, the device 1000 may be withdrawn from the patient's body. If further treatment is desired, the device 1000 may be withdrawn to a position for a new treatment. Instead of withdrawing the device 1000, the operator also has the alternative of advancing the device 1000 further into the body of the patient with the aid of the guide wire segment 1023, until the distal end 1027 of the guide wire segment 1023 is distal to a new treatment area, whereafter a new treatment can be performed.

Figure 12:
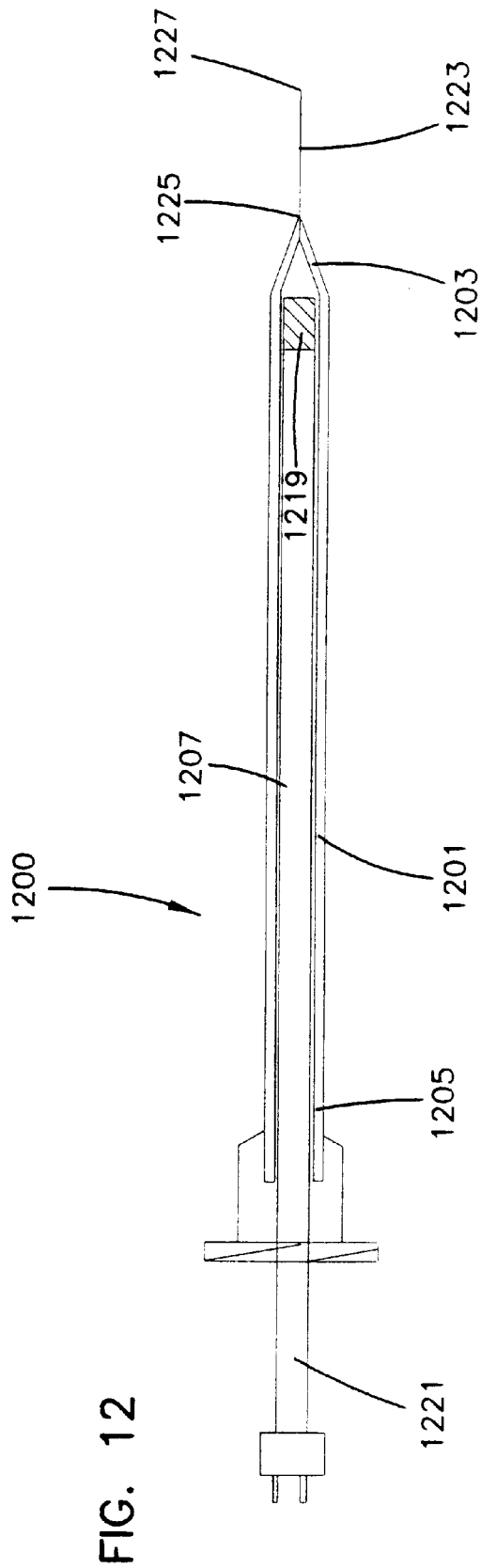
FIG. 12 is a schematic side view in cross-section of a sixth embodiment of an X-ray treatment device in accordance with the invention.

A sixth embodiment of the device according to the invention is shown in FIG. 12. The device 1200 includes a sheath 1201 having a distal end 1203 and a proximal end 1205. A wall of the sheath 1201 defines a primary lumen 1207 longitudinally through the sheath 1201. An X-ray emitter 1219 is fixed in the primary lumen 1207 near the distal end 1203 of the sheath 1201. The X-ray emitter 1219 is coupled to a cable 1221. The device 1200 further includes a guide wire segment 1223 coupled to the sheath 1201 or to the emitter 1210. The guide wire segment 1223 may be formed from many different materials. For example, the guide wire segment 1223 may comprise a tightly wound coil of a metallic material, making it steerable through vessels in the patient's body. The guide wire segment 1223 does not take up space inside the primary lumen 1207 and does not shadow an annular radiation pattern from the X-ray emitter 1219. The guide wire segment 1223 includes a proximal end 1225 and a distal end 1227, and the proximal end 1225 is coupled to distal end 1203 of the sheath 1201.

In using the sixth embodiment, the sheath 1201 is moved through the passage inside the patient's body so that the distal end 1203 is distal to the treatment area. In this embodiment, the X-ray emitter 1219 is fixed within the primary lumen 1207, near the distal end 1203.

Figure 20:
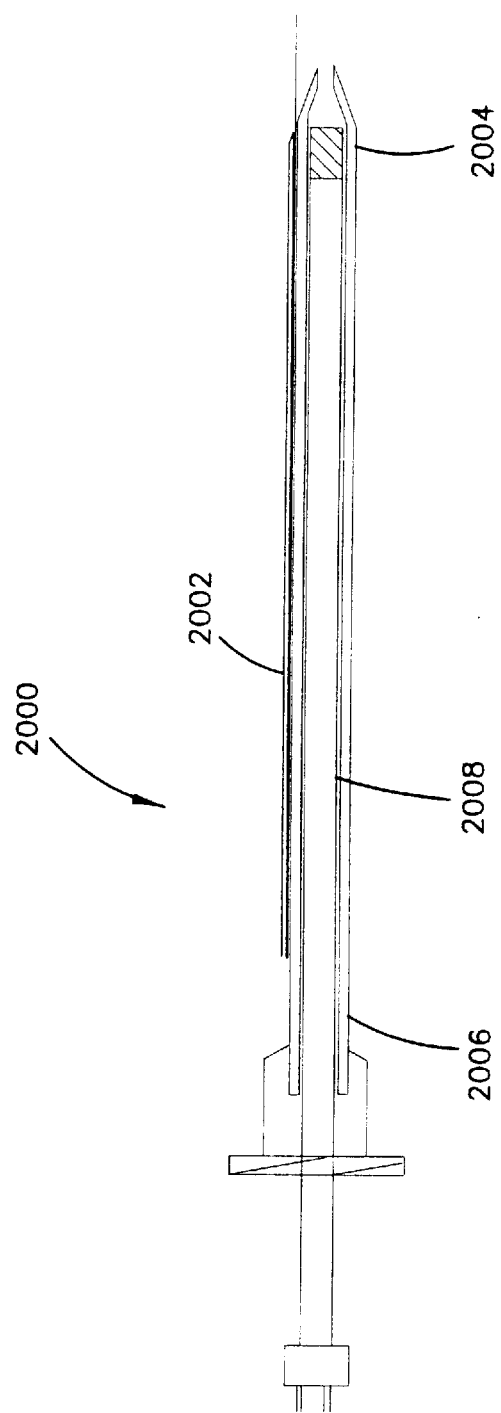
FIG. 20 is a side view in cross-section of a seventh embodiment in accordance with the invention.

FIG. 20 illustrates a device 2000 comprising a parking lumen 2002 that extends from a distal end 2004 of the sheath to a proximal end 2006. Such a parking lumen 2000 has advantages in ease of use. The guide wire may be situated in the parking lumen 2002 simultaneously with the emitter being in the primary lumen 2008, and the guide wire cannot slip out of the parking lumen during positioning as is possible with the partial parking lumen of the other embodiments.

After using the X-ray emitter 1219, the device 1200 may be withdrawn from the patient's body. If further treatment is desired, the device 1200 may be withdrawn to a position for a new treatment. Instead of withdrawing the device 1200, the operator also has the alternative of advancing the device 1200 further into the body of the patient with the aid of the guide wire segment 1223 for maneuverability. The device 1200 may be advanced until the distal end 1227 of the guide wire segment 1223 is distal to a new treatment area, and a new treatment can be performed.

In using any of the above embodiments of the device according to the invention, the X-ray emitter will be used to emit X-ray radiation. This may involve, for example, accelerated electrons emitting Bremsstrahlung upon impinging on a cathode in the X-ray emitter. As known in the art and described in application Ser. No. 08/701,764, only a fraction of the kinetic energy of the electrons will be emitted as X-ray radiation. Heat may be generated in the X-ray emitter and dissipate from it. A cooling mechanism for the X-ray emitter may therefore be desired. The normal blood flow in a blood vessel will usually carry away any heat generated, but providing a coolant flush, for example saline, controllable by the operator is preferable since it presents a more reliable cooling mechanism. Thus, a coolant fluid may be delivered in the sheath over the surface of the X-ray emitter. The coolant may be pre-cooled to increase its cooling capacity. A biocompatible coolant fluid, such as saline solution, may exit the sheath at its distal end such that new fluid may continuously be delivered to the emitter. Another method of cooling is to provide a sac with coolant fluid around the emitter. Valve adapters may be used for introducing the coolant fluid into the sheath and maintaining it inside the sheath.

Where cooling fluid is circulating between the sheath and the emitter, a fluid seal is desirable between the cable and the sheath at the proximal end of the X-ray device in order to enable the maintenance of a pressurized fluid flow within the sheath. However, in some embodiments of the X-ray device, the cable must be permitted to move relative to the sheath when the X-ray emitter is withdrawn and advanced in the sheath.

Figure 13:
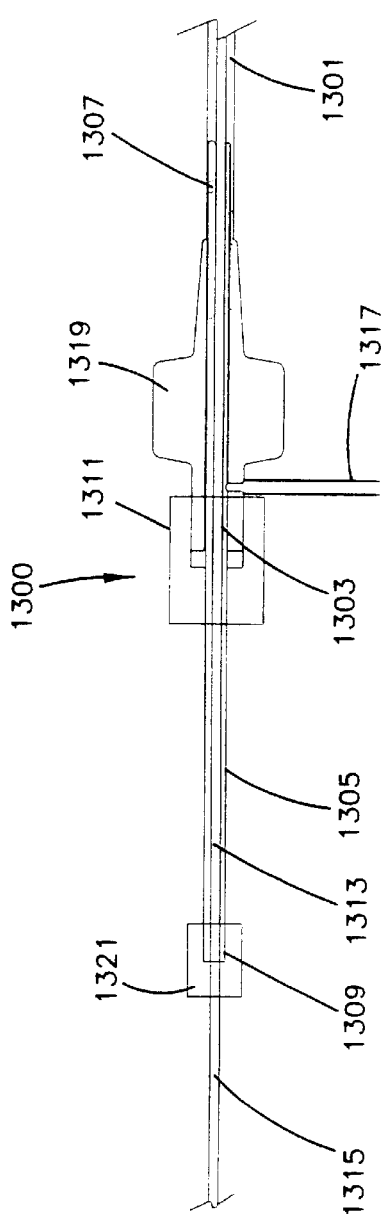
FIG. 13 is a schematic side view in cross-section of an embodiment of a hemostasis valve adapter in accordance with the invention.

An embodiment of a hemostasis valve adapter according to the invention is shown in FIG. 13. The valve adapter 1300 includes catheter sheath 1301, and a cable support tube 1305, that has a distal end 1307 and a proximal end 1309. The distal end 1307 and a portion of the cable support tube 1305 are inside the catheter sheath 1301. A seal device 1311 is positioned on the proximal end 1303 of the catheter sheath 1301. The seal device 1311 seals between the catheter sheath 1301 and the cable support tube 1305, while the cable support tube 1305 is movable through the seal device 1311. The seal device 1311 may be used with several different configurations and materials. For example, the seal device 1311 may comprise an elastomeric disk with a central opening for the cable support tube 1305. The cable support tube 1305 includes a lumen 1313 which contains a portion of a cable 1315. The cable 1315 may be connected to, for example, an X-ray device (not shown). The cable support tube 1305 may be affixed to a portion of the cable 1315, for example at the proximal end of the support tube 1305.

The valve adapter 1300 may comprise a fluid valve or port 1317, for inserting coolant fluid into the catheter sheath 1301. The fluid valve may be connected to a tank with cooling fluid. A device may be connected between the fluid valve and the tank for pressurizing the fluid and/or controlling the flow amount. Different coolant fluids may be used. For example, saline may be flushed through the fluid valve 1317 into the catheter sheath 1301. Although the fluid valve 1317 is illustrated at the proximal end of the catheter, it could also be positioned at other locations along the cable support tube 1305.

The valve adapter 1300 may further comprise a proximal pullback adapter 1319 sealed onto the proximal end 1303 of the catheter sheath 1301, to allow for attachment to a pullback assembly. The seal device 1311 may be fitted onto the proximal pullback adapter 1319. The valve adapter 1300 may further comprise a distal pullback adapter 1321, sealed onto the proximal end 1309 of the cable support tube 1305, to allow for attachment to a pullback assembly. The distal pullback adapter 1321 and the proximal pullback adapter 1319 may be used in retracting or advancing the cable and the X-ray emitter through the catheter sheath 1301. For example, the proximal pullback adapter 1319 and the distal pullback adapter 1321 may be mounted on the body and the carriage, respectively, of a catheter pullback assembly according to the invention. The fluid valve 1317 may be mounted on the adapter 1319 for inserting coolant fluid into the catheter sheath 1301.

The embodiment of the hemostasis valve adapter may be used, for example, by inserting the cable 1315, connected to an X-ray emitter, into the cable support tube, and inserting the cable support tube and the X-ray emitter into the catheter sheath 1301. The catheter sheath 1301 may already have been placed in the passage in the patient's body, where X-ray treatment is to be performed. A coolant fluid may be introduced into the catheter sheath 1301 through the fluid valve 1317. The seal device 1311 seals between the cable support tube 1305 and the proximal end of the catheter sheath 1301. The cable 1315 and the cable support tube 1305 may be moved with respect to the catheter sheath 1301 during the X-ray treatment process.

Figure 14:
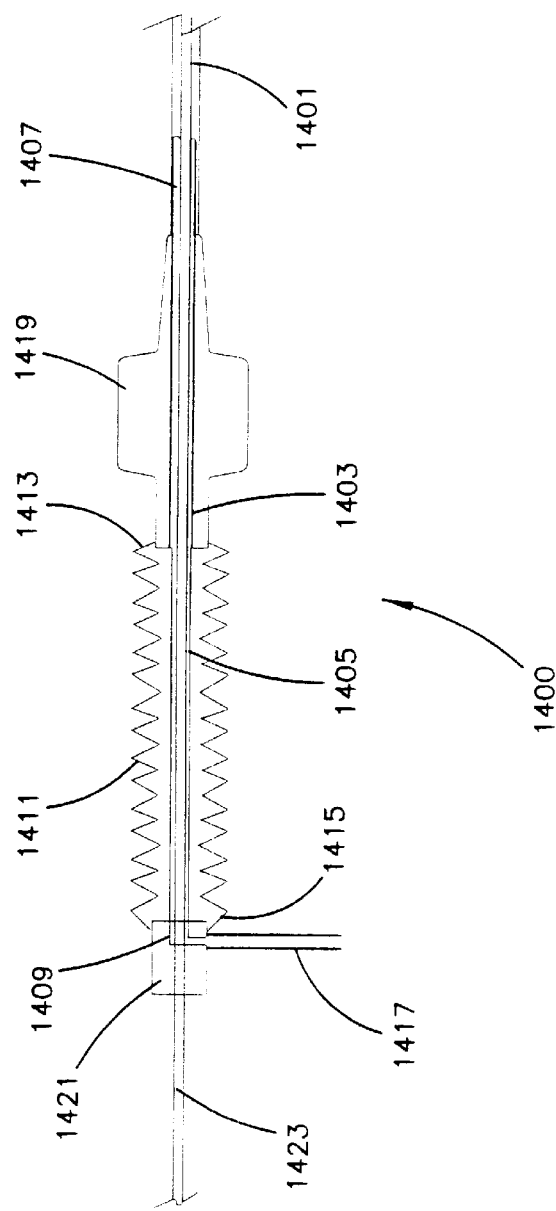
FIG. 14 is a schematic side view in cross-section of an embodiment of a bellows valve adapter in accordance with the invention.

An embodiment of a bellows valve adapter according to the invention is shown in FIG. 14, that may be used in place of the hemostasis valve adapter, to provide a seal and allow movement of the cable. The adapter 1400 includes a catheter sheath 1401 with a proximal end. The adapter 1400 further includes a cable support tube 1405 with a distal end 1407 and a proximal end 1409. A cable 1423 may be inserted into the cable support tube 1405 and into the catheter sheath 1401. The cable 1423 may be connected to, for example, an X-ray device. The cable support tube 1405 will be used, for example, to support the cable 1423. The cable support tube 1405 may be formed from a number of materials. The distal end 1407 and a portion of the cable support tube 1405 are inside the catheter sheath 1401. The adapter 1400 further includes a bellows 1411 comprising a collapsible tube with a first end 1413 and a second end 1415. A collapsible accordion tube is shown in the embodiment, but different kinds of collapsible tubing may be used with the invention. For example, an essentially cylindrical collapsible tubing or a collapsible telescope-shaped tubing may be used. The first end 1413 is connected to the proximal end 1403 of the luer fitting 1419 either permanently or removably. The second end 1415 is connected to the proximal end 1409 of the cable support tube 1405. The valve adapter 1400 may further comprise a fluid valve 1417 for inserting coolant fluid into the bellows 1411 and the catheter sheath 1401. The fluid valve 1417 may be located adjacent the proximal end 1409 of the cable support tube 1405 in FIG. 14, and may be located in other places along the cable support tube. When biocompatible coolant fluids are being used, the catheter 1401 may have an opening at its distal end for letting out coolant fluid.

The valve adapter 1400 may further comprise a distal pullback adapter 1421, sealed onto the proximal end 1403 of the catheter sheath 1401, for attachment to a pullback assembly. The valve adapter 1400 may further comprise a proximal pullback adapter 1419, sealed onto the proximal end 1409 of the cable support tube 1405, for attachment to a pullback assembly. An embodiment comprising the distal pullback adapter 1419 and the proximal pullback adapter 1421 may have the first end 1413 of the bellows 1411 sealed onto the proximal pullback adapter 1419 and the second end 1415 of the bellows 1411 sealed onto the distal pullback adapter 1421. In this embodiment, the fluid valve 1417 may be situated on the pullback adapter 1421 for inserting coolant fluid into the bellows 1411 and the catheter sheath 1401. Alternatively, the fluid valve 1417 may be situated on the proximal pullback adapter 1419.

In using the embodiment of the bellows valve adapter, the catheter sheath 1401 with an X-ray emitter coupled to the cable 1423 is positioned in a passage within the patient's body, so that a distal end of the catheter sheath 1401 is at a distal end of the treatment area. The treatment area may then be exposed to X-ray radiation by supplying high voltage to the X-ray emitter through the cable 1423. If it is desired to perform X-ray treatment on several portions of the treatment area, the X-ray emitter and the cable 1423 may be withdrawn inside the catheter sheath 1401. Coolant fluid may be provided through the fluid valve 1417 into the bellows 1411 and catheter sheath 1401. The bellows 1411 allows the cable 1423, the pullback adapter 1421, and the cable support tube 1405, to be withdrawn from their initial position inside the catheter sheath 1401. The length and/or configuration of bellows 1411 may be chosen in consideration of how far the cable, the pullback adapter, and the cable support tube will be withdrawn from their initial positions during the treatment. The distal pullback adapter 1419 and the proximal pullback adapter 1421 may, for example, be mounted on a catheter pullback assembly in accordance with the invention. In such an embodiment, the proximal pullback adapter 1421 may be mounted on the movable carriage of the catheter pullback assembly and the distal pullback adapter 1419 may be mounted on the stationary body of the catheter pullback assembly.

A uniform radiation pattern is desired in many situations, such as where a blood vessel has been dilated and an annular radiation pattern is needed to prevent restenosis uniformly around the interior surface of a portion of the blood vessel. In order to provide a uniform radiation pattern, centering the X-ray emitter within the blood vessel or other passage is desired. One centering device that may be included with the X-ray device of the present invention is a balloon that runs at least the length of the emitter, surrounding the shaft. The balloon may have longitudinal flutes molded into the exterior surface. When contacting the passage wall, the flutes may define passages for blood flow. This centering technique and device are described in U.S. Pat. No. 5,643,171, which is hereby incorporated herein by reference. Other centering devices are contemplated by this invention, some of which are also described in U.S. Pat. No. 5,643,171.

In many body passages, a dilation and centering structure is desirable to expand a passage that is normally in a collapsed state so that a uniform pattern of radiation may be achieved. One type of dilation structure may include an inflatable balloon at the distal end of the sheath, surrounding the X-ray emitter, as described in U.S. Patent Application titled "DEVICE FOR DELIVERING LOCALIZED X-RAY RADIATION TO AN INTERIOR OF A BODY AND METHOD OF MANUFACTURE," filed on Feb. 20, 1998, which is hereby incorporated by reference herein.

Figure 15:
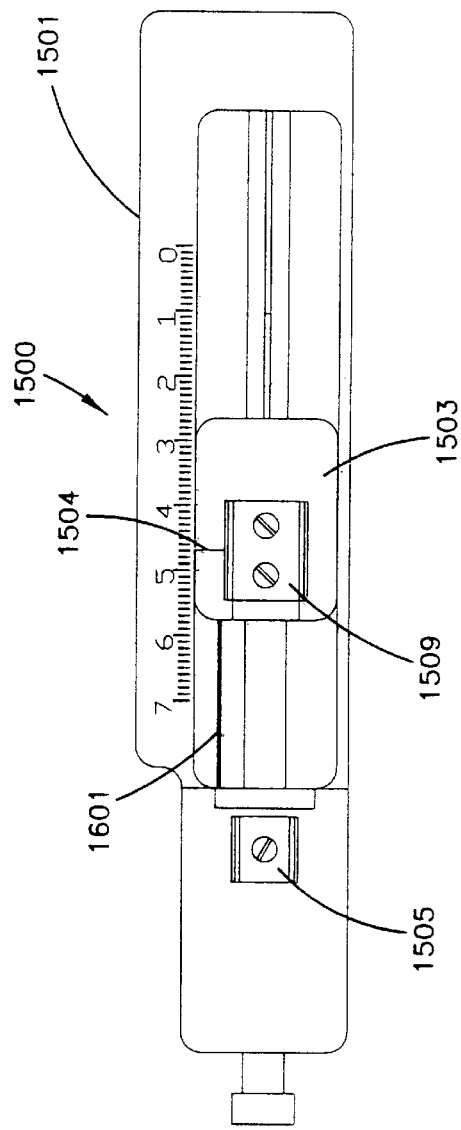
FIG. 15 is a top view of a part of an embodiment of a catheter pullback assembly in accordance with the invention.
Figure 16:
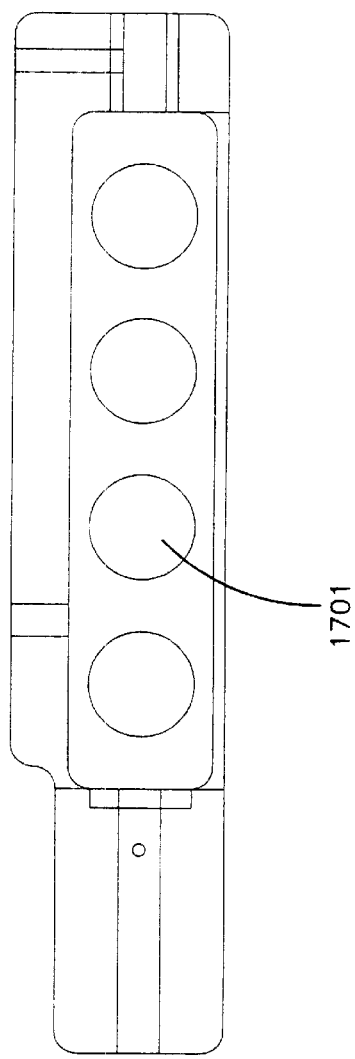
FIG. 16 is an exploded top view of a part of an embodiment of a catheter pullback assembly in accordance with the invention.
Figure 17:
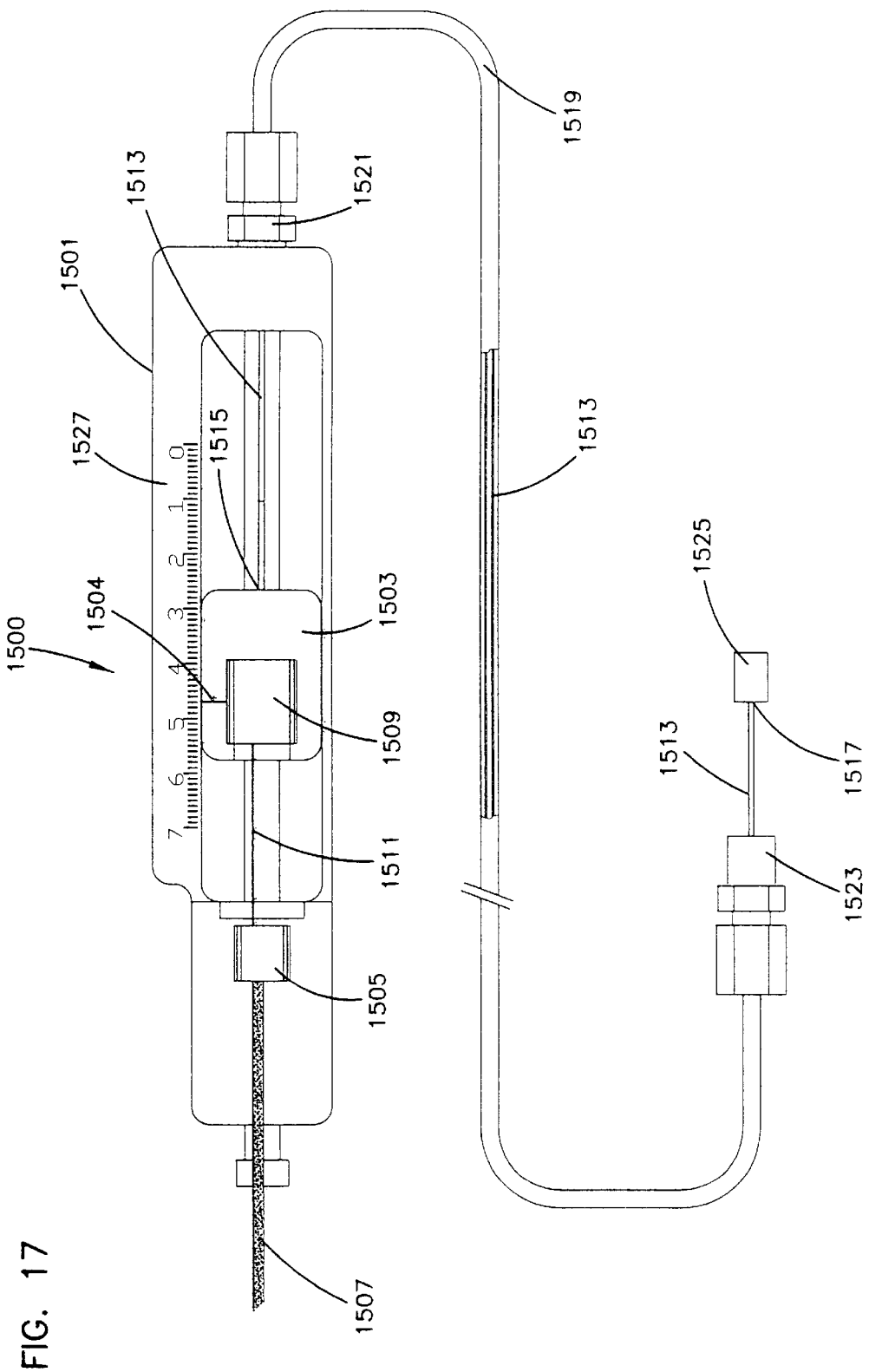
FIG. 17 is a bottom view of a part of an embodiment of a catheter pullback assembly in accordance with the invention.

An embodiment of the catheter pullback assembly in accordance with the invention is shown in FIGS. 15–17. The catheter pullback assembly is a reusable device, which may be used to move a catheter through a treatment zone, whereby a treatment area is exposed to X-ray radiation. The catheter pullback assembly 1500 may include a body 1501 and a carriage 1503 mounted on the body 1501. The carriage 1503 is slidable with respect to the body 1501. This can be accomplished in a number of different ways. For example, the carriage 1503 may be provided with a groove underneath it, where the groove mates with a rail on the body 1501, whereby the carriage 1503 may slide on the body 1501. The assembly 1500 further includes a distal pullback adapter 1505 mounted on the body 1501, and connected onto a proximal end of a catheter sheath 1507. The assembly further includes a proximal pullback adapter 1509 mounted on the carriage 1503. The pullback adapter 1509 is sealed onto a cable 1511 which may be positioned inside the catheter sheath 1507. The cable 1511 typically extends also on the other side of the proximal pullback adapter 1509 (not shown), to enable connection of the cable 1511 to a voltage source, for example.

The catheter pullback assembly 1500 may further comprise an actuating cable 1513 having a proximal end 1515 and a distal end 1517. The proximal end 1515 may be attached to the carriage 1503. A conduit 1519 may surround a portion of the actuating cable 1513. The conduit 1519 has a distal end 1521 and a proximal end 1523. The distal end 1521 is attached to the body 1501 of the pullback assembly 1500. The catheter pullback assembly 1500 may further comprise a cable connector 1523 attached to a proximal end 1517 of the actuating cable 1513. The cable connector 1523 may be used for connecting the actuating cable 1513 to a motor means, whereby the carriage 1503 and the actuator cable 1513 may be actuated. For example, the cable connector 1523 may connect magnetically to the motor means, whereby connecting and disconnecting may be performed easily, yet providing a secure connection between the cable connector and the motor means. The proximal end 1523 of the conduit 1519 may be attached to a stationary location on the control unit, so that the actuating cable 1513 moves relative to the conduit 1519 when the motor means are activated.

The catheter pullback assembly may further comprise means for sealing between the catheter sheath 1507 and the cable 1511. The means for sealing may comprise a fluid valve for inserting coolant fluid into the catheter sheath 1507. Such means may include, for example, a hemostasis valve adapter, as described above. In such an embodiment, the catheter pullback assembly 1500 may comprise a seal on the adapter 1505 for sealing the adapter 1505 to the cable 1511, such that the cable 1511 is movable with respect to the adapter 1505. As noted above, the seal may comprise many different configurations and may, for example, be an elastomeric disk with a central opening for the cable.

Another alternative is that the catheter pullback assembly 1500 may be provided with a bellows valve adapter substantially as described above. In this embodiment the assembly further includes a bellows comprising a collapsible tube with a first and second end. The first end of the bellows is connected to the adapter 1505 and the second end of the bellows is connected to the pullback adapter 1509.

The catheter pullback assembly 1500 may further comprise an elastic band 1601, as illustrated in FIG. 15. The elastic band may be attached to the carriage 1503 and to a point on the body 1501 adjacent to the adapter 1505. Many different elastic bands may be used with this embodiment. The length and/or resilience of the elastic band 1601 may be selected such that the carriage 1503 may be fully withdrawn on the body 1501 using the motor means, thus stretching the elastic band 1601. The elastic band 1601 biases the carriage 1503 towards the adapter 1505. The elastic band may help prevent 15 the cable 1511 from being inadvertently withdrawn from the catheter sheath 1507 and provides tension to ensure smooth movement.

The bottom of the body 1501 may comprise one or more holes 1701 as illustrated in FIG. 17. The holes 1701 may be useful to allow draining or any fluid leaking from the catheter sheath, valve, or elsewhere, such as blood or saline, so the movement of the carriage is not impaired. The holes may also be used in securing the catheter pullback assembly 1500 to a table-top surface or the like other securement devices can also be used, but are not required.

The catheter pullback assembly may comprise means for indicating how far the catheter is moved through the treatment area. For example, the body 1501 may be provided with travel indicator markings 1527. A mark on the carriage 1503 will indicate how far the X-ray emitter has been withdrawn since the beginning of the treatment session.

In using a catheter pullback assembly according to the invention, the catheter sheath containing the cable 1511 and an X-ray emitter, is positioned in a passage within the patient's body substantially as described above. The cable connector 1525 may be connected to a motor means for actuating the actuator cable 1513. The proximal end 1523 of the conduit 1519 may be connected so that it is fixed with respect to the motor means actuating the actuator cable 1513. The conduit 1519 thereby may allow the actuating force from the motor means to be transmitted to the carriage and the X-ray emitter without the body 1501 sliding due to the actuating force. It may also facilitate positioning the motor means such that the actuating cable 1513 has a non-straight configuration between its distal end 1515 and its proximal end 1517. When the cable connector 1525 is retracted by the motor means, the actuating cable 1513 will move the carriage 1503 on the body 1501. The pullback adapter 1509 will withdraw the cable 1511 and the X-ray emitter inside the catheter sheath 1507. The elastic band 1601 will be stretched out as the X-ray emitter is withdrawn, biasing the carriage towards the adapter 1505. A mark on the carriage 1503 may indicate on the travel indicator 1527 how far the cable 1511 and the X-ray emitter have been withdrawn.

The typical X-ray emitter used in connection with the present invention is about 5 to 7 mm in length. It is anticipated that as the emitter operates, about an equivalent length of the patient passage is treated.

Figure 18:
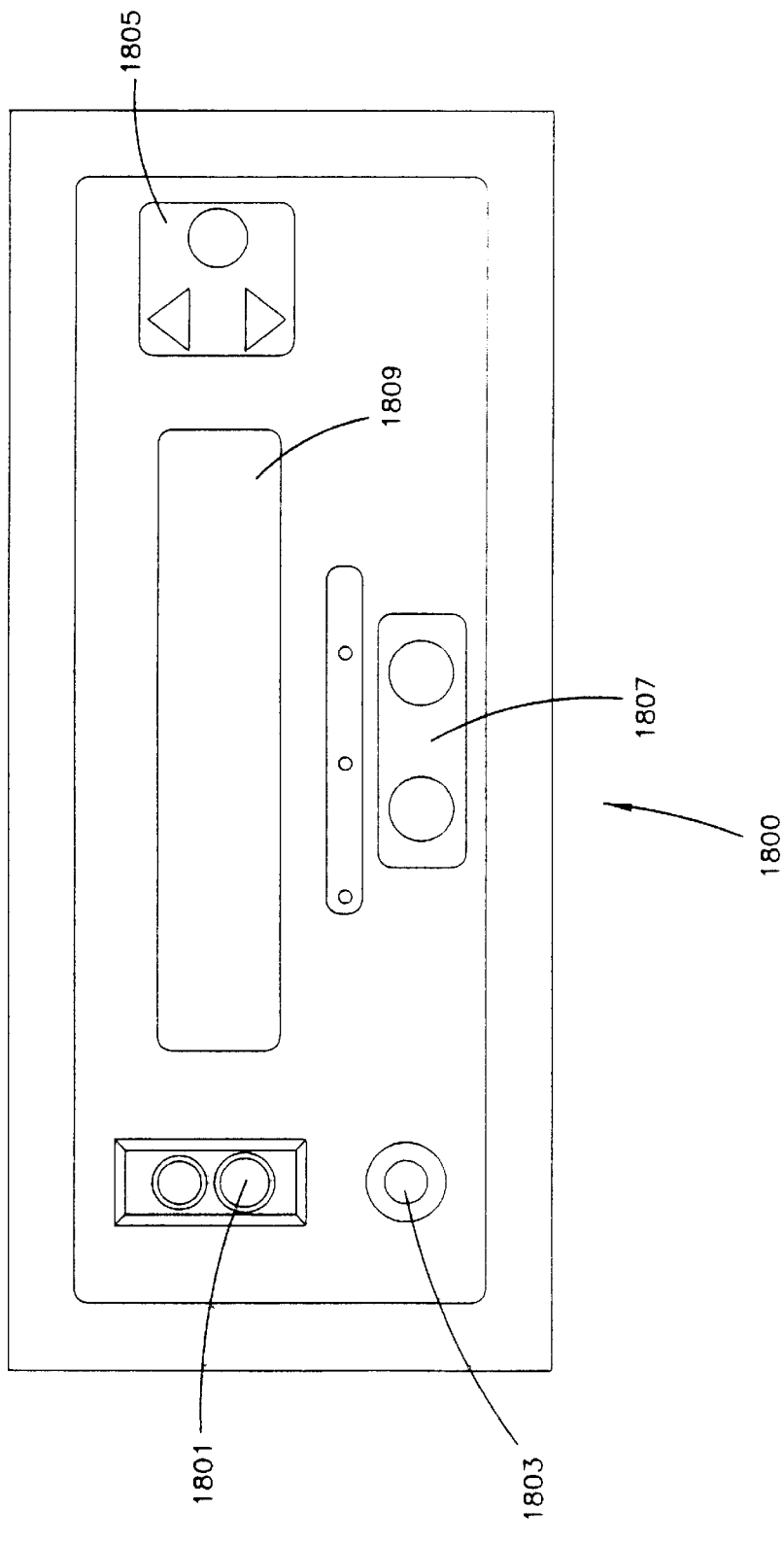
FIG. 18 is a front view of a part of an embodiment of a control unit in accordance with the invention.

An embodiment of a control unit according to the invention is shown in FIG. 18. The control unit 1800 may typically be used to provide a high voltage/low current power supply to the X-ray catheter of the invention. The control unit may also be used to control the catheter pullback assembly according to the invention. For these purposes the control unit 1800 may comprise well-known means such as voltage sources, current sources and stepping motors and various input means for setting the operating parameters of the described components. The control unit 1800 includes a high-voltage output 1801. A cable connected to the X-ray emitter may be connected to the high voltage output 1801 for producing X-ray radiation during treatment. The control unit 1800 includes a pullback outlet 1803. The pullback outlet 1803 may be used to withdraw the X-ray emitter inside the catheter as a part of the treatment. For example, the cable connector 1525 of the catheter pullback assembly 1500 may be attached to the pullback outlet 1803, whereby the X-ray emitter may be withdrawn within the catheter sheath using the catheter pullback assembly.

The control unit 1800 includes input means 1805 for inputting or altering operational parameters to be used in the treatment. For example, the input means may include an "up" button for increasing a displayed value, a "down" button for decreasing a displayed value, and an "enter" key for entering a displayed value. The control unit may be provided with internal memory means storing upper and lower limits for one or more of the operation parameters. The operator may choose an operating parameter within the upper and lower limit of that parameter.

The control unit 1800 may further comprise output means for outputting operational parameters to be stored. For example, the control unit 1800 may output operational parameters to a data key, similar to the data key 119 shown in FIG. 1. The data key may then, for example, be used to store actual operational parameters on a storage device, for example a PC.

The control unit 1800 includes control means, whereby the operator may control the treatment process. For example, the control means 1800 may include a "start" button for initiating the treatment session and an "abort" button for interrupting the treatment.

A display 1809 may be provided, for displaying operational parameters and/or prompting the operator to input parameters. Additionally, the display 1809 may display system messages such as warnings and confirmation questions.

Figure 19:
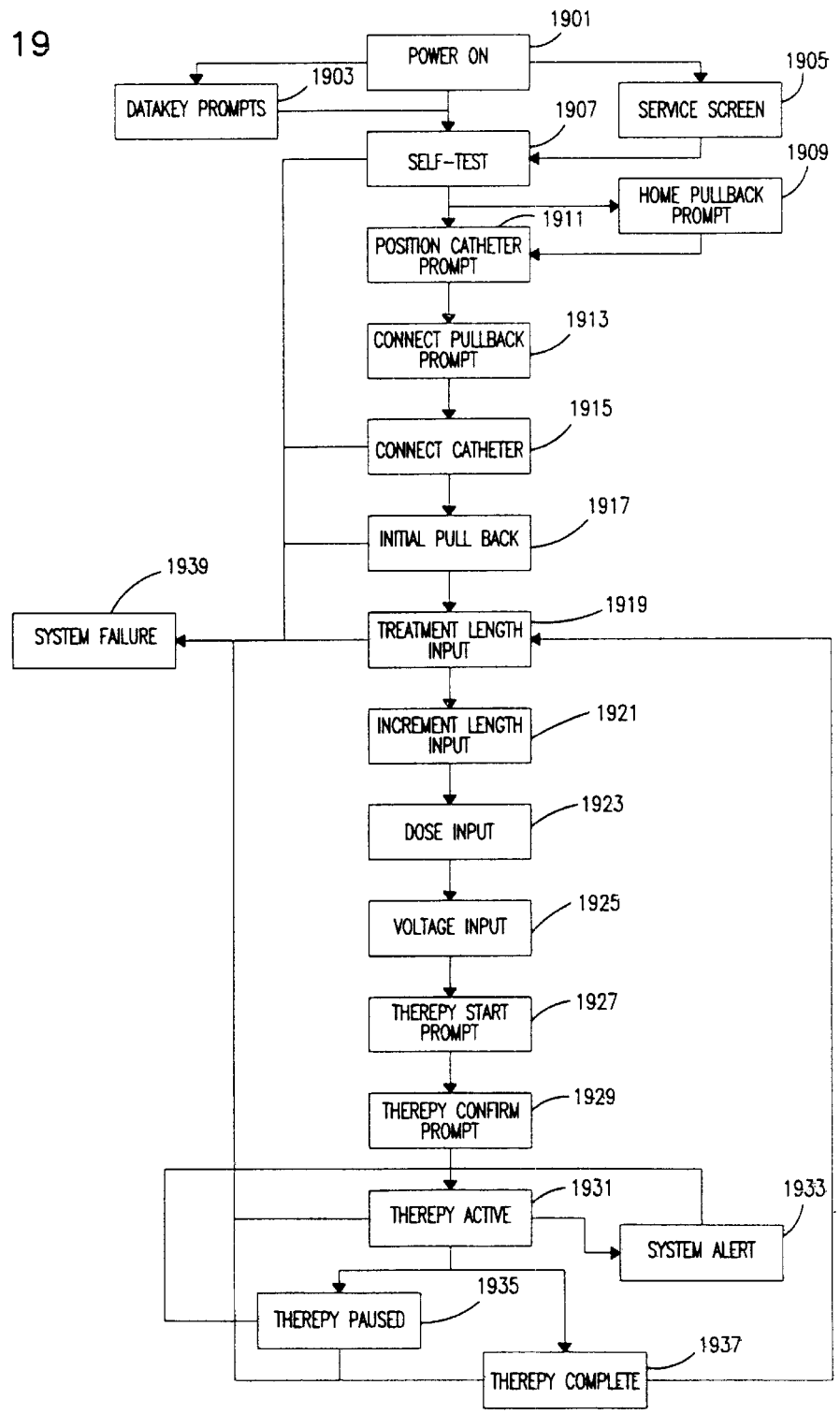
FIG. 19 is a display screen flowchart for an embodiment of a control unit in accordance with the invention.

A flowchart for the operation of an embodiment of the control unit of the invention is shown in FIG. 19. In step 1901 the operator turns on the control unit. This may be performed, for example, by pressing a power button on the control unit. There may be visual and audio feedback to confirm that the control unit has been turned on. In step 1903 the control unit expects a data key to have been inserted into the control unit. If a data key has not been inserted a screen will be displayed prompting the operator to insert a data key. If a data key has been inserted that, for any of a number of reasons, cannot be used, the control unit will display a screen informing the operator about this.

In step 1905 the control unit displays a service screen indicating any service needs. In step 1907 the control unit performs a self test. During the self test the control unit initiates a diagnostic software and hardware check to verify that all control unit systems are operating properly. Throughout the procedure the software is continuously monitored to verify microprocessor control. If the pullback outlet is not reset to its home position, the control unit will display a screen informing the operator about this at step 1909. The operator may then have a choice, for example, between resetting the pullback outlet to its home position or proceeding with the pullback outlet in its current position.

In step 1911 the control unit prompts the operator to position the catheter in its initial position before X-ray treatment. For example, the catheter may be positioned with its distal end distal to the treatment area in a passage inside a patient's body. As discussed above, the X-ray catheter may be provided with a radiopaque marker whereby its position can be determined using fluoroscopy.

In step 1913 the control unit prompts the operator to connect the catheter pullback assembly to the control unit and to connect the distal pullback adapter on the X-ray cable to the catheter pullback assembly.

In step 1915 the control unit prompts the operator to connect the X-ray catheter to the control unit. This may be done, for example, by connecting a cable coupled to the X-ray emitter to the high voltage outlet of the control unit.

In step 1917 the control unit prompts the operator to retract the catheter to the start of the treatment zone in the passage within the patient's body. This may be done, for example, by the operator pressing a "start" button on the control unit whereby the X-ray catheter is slowly retracted. When the catheter reaches the start of the treatment area the operator may release the button.

In step 1919 the control unit prompts the operator to input the length of the treatment area. One embodiment of the catheter pullback assembly allows treatment areas to have lengths in the range between 0 and 7 cm, for example.

In step 1921 the control unit prompts the operator to input the desired increment length. The increment length is the distance that the X-ray emitter will be retracted from one area of therapy to the next. The increment length may be held constant throughout the treatment zone. For example, the operator may enter a value in millimeters which will be the increment length of the therapy session. In the alternative, the operator may choose a constant rate of movement for the X-ray emitter.

In step 1923 the control unit prompts the operator to enter the desired dose of X-ray radiation to be irradiated for each increment. A physician will determine the desired dose to be used in the X-ray treatment, depending on a number of characteristics of the patient and the medical condition that is to be treated. The operator may select the desired dose by entering a desired value for example in Grays, or by Coulombs, an indirect measure of the dose, to be delivered during the X-ray treatment. For example, the charge transported through the X-ray emitter during treatment, measured in Coulombs, is a measure of the X-ray radiation that has been irradiated to the treatment area. The operator may input a value in Coulombs to indicate the desired dose per increment.

In step 1925 the control unit prompts the operator to enter the desired therapy voltage. The therapy voltage applied to the X-ray emitter determines the wavelength characteristics of the X-ray emission that is irradiated. The operator will determine the desired characteristics of the X-ray radiation and set the desired therapy voltage accordingly. For example, the operator may input a desired therapy voltage as a number of kilovolts to be used in the therapy session.

In step 1927 the control unit prompts the operator to review the operating parameters input during steps 1919–1925. The inputted parameters may be displayed on the display of the control unit and the operator may indicate by pressing a button that the parameters are acceptable. If one or more input parameter is to be changed the operator may indicate so by pressing another button, for example.

In step 1929 the control unit prompts the operator to confirm the setting of the operating parameters reviewed in step 1927. For example, the operator may be prompted to either press one button to confirm and thereby start the therapy session, or to press another button to reset the operating parameters entered in steps 1919–1925.

In step 1931 the X-ray therapy session is active. The X-ray emitter is producing X-ray radiation and the control unit retracts the X-ray emitter by the input increment after the input dose has been reached. This step is repeated throughout the input length of the treatment area. The control unit may display information as to how much of the X-ray therapy session has been completed.

The operator may pause the therapy session by pressing a button on the control unit as indicated by step 1935. After pausing the therapy session the operator has a choice, for example, between continuing the therapy session and stopping the therapy session.

When the whole length of the treatment area has been treated with X-ray radiation the control unit may inform the operator that the therapy is complete as in step 1937.

If during any of the above referenced steps the control unit experiences a system fault it will display a screen informing the operator about the system failure as in step 1939.

It is to be understood that even though numerous characteristics and advantages of the invention have been set forth in the foregoing description, together with details of the structure and function of the invention, the disclosure is illustrative only and changes may be made in detail, especially in matters of shape, size and arrangement of the parts within the principles of the invention to the full extent indicated by the broad general meaning of the terms in which the appended claims are expressed.

What is claimed is:

1. A device suitable for X-ray treatment in a passage within a body of a patient, comprising:
    a sheath comprising a wall, a proximal end, a distal end and a distal opening at the distal end, the sheath defining a primary lumen longitudinally through the sheath, the sheath further comprising a parking lumen adjacent to a portion of the primary lumen and having a proximal end and a distal end, the distal end of the parking lumen having an opening to the primary lumen and the proximal end of the parking lumen having an opening to the exterior of the sheath; and
    an X-ray emitter coupled to a cable, positionable within the primary lumen so that the X-ray emitter can be positioned near the distal end of the sheath.

2. The device of claim 1, further comprising a guide wire, having a proximal end and a distal end.

3. The device of claim 1, the sheath further comprising a stiff pushable material.

4. The device of claims 1, the X-ray emitter being moveable within the primary lumen.

5. The device of claim 1 and further comprising a stylet defining a stylet lumen, and the stylet positionable within the primary lumen, the stylet comprising a supporting material.

6. The device of claim 1, the sheath comprising a stiff, pushable material.

7. The device of claim 1, further comprising a stylet defining a stylet lumen, the stylet lumen positionable within the primary lumen, the stylet comprising a material stiffer than the sheath.

8. The device of claim 1, the sheath further comprising a most distal portion and a second most distal portion, the parking lumen being defined through the second most distal portion of the sheath.

9. The device of claim 1, wherein the sheath is formed by multi-lumen extrusion of the parking lumen and the primary lumen.

10. The device of claim 1, wherein the X-ray emitter and cable are within the primary lumen.

11. The device of claim 1, the X-ray emitter being movable within the primary lumen.

12. The device of claim 1 wherein the parking lumen extends from the distal end of the sheath to the proximal end of the sheath.

13. The device of claim 1, the sheath further comprising a fluid port near the proximal end of the sheath for introducing fluid into the sheath, having a distal opening for allowing fluid to exit from the sheath.

14. The device of claim 1, the sheath further comprising a reinforcing section near to the distal end of the sheath, the reinforcing section comprising a stiffening material.

15. The device of claim 1, the sheath further comprising a proximal section comprising a stiffer material than a remainder of the sheath.

16. The device of claim 1, the sheath further comprising a hemostasis valve capable of creating a seal around the cable.

17. The device of claim 1, the device further comprising a guide wire segment coupled to the distal end of the sheath.

18. The device of claim 17, the X-ray emitter being movable within the primary lumen.

19. The device of claim 17, the X-ray emitter being fixed within the primary lumen near the distal end of the sheath.

20. The device of claim 17, the guide wire segment being coil shaped.

21. The device of claim 1, the X-ray emitter being fixed within the sheath near the distal end of the sheath, the device further comprising a guide wire segment coupled to the X-ray emitter and extending beyond the distal end of the sheath.

22. The device of claim 1, the sheath further comprising at least one radiopaque marker at the distal end of sheath.

23. The device of claim 1 the X-ray emitter further comprising a housing having at least one radiopaque marker.

24. The device of claim 1, the proximal end of the sheath further comprising a valve capable of creating a seal around the cable, where the cable is movable with respect to the seal.

25. The device of claim 1, the sheath comprising a polymer material.

26. The device of claim 1, the sheath comprising a polymer composite and a metallic material.

27. The device of claim 1, the sheath comprising a metallic material.

28. The device of claim 1, further comprising a centering device at the distal end of the sheath.

29. The device of claim 1, the wall of the sheath further comprising an interior surface at the distal end of the sheath, the interior surface comprising raised portions that support the X-ray emitter to permit fluid flow between the wall and the X-ray emitter.

30. A device suitable for X-ray treatment in a passage within a body of a patient, comprising:

a sheath comprising a wall, a proximal end, and a distal end, the sheath wall defining a primary lumen longitudinally through the sheath and defining a parking lumen adjacent to a portion of the primary lumen, a distal end of the parking lumen having an opening to the primary lumen and a proximal end of the parking lumen having an opening to the exterior of the sheath; and an X-ray emitter coupled to a cable, positionable within the primary lumen so that the X-ray emitter is near the distal end of the sheath.

31. The device of claim 30, the sheath further comprising a most distal portion and a second most distal portion, the parking lumen being defined through the second-most distal portion of the sheath.

32. The device of claim 30, the X-ray emitter being movable within the primary lumen.

33. The device of claim 30, where the distal end of the parking lumen is about 1 cm proximal to the distal end of the sheath.

34. A method for positioning an X-ray emitter at a treatment area in a passage within a body of a patient, comprising:

moving a guide wire, having a proximal end and a distal end, through the passage so that the distal end is distal to the treatment area;

advancing a sheath, the sheath comprising a proximal end and a distal end, defining a primary lumen extending longitudinally through the sheath and a parking lumen adjacent to a portion of the primary lumen and having a proximal end and a distal end, the distal end of the parking lumen having an opening to the primary lumen and the proximal end of the parking lumen having an opening to the exterior of the sheath, the sheath being advanced by inserting the guide wire into the distal end of the primary lumen and into the parking lumen so that the distal end of the sheath is distal to the treatment area;

withdrawing the guide wire until the distal end of the guide wire is situated inside the parking lumen of the sheath, after the sheath is advanced; and placing the X-ray emitter at the distal end of the sheath within the primary lumen.

35. The method of claim 34, wherein the step of moving the guide wire comprises following turns of a blood vessel.

36. The method of claim 34, the primary lumen comprising a most distal portion and a second most distal portion, the parking lumen being defined through the second most distal portion, the step of placing the X-ray emitter comprising moving the X-ray emitter from a proximal portion to the most distal portion of the primary lumen.

37. A method of exposing a length of a treatment area in a patient to X-ray radiation using an X-ray emitter being coupled to a connector at a distal end of the connector, the method comprising:

providing a carriage slidably mounted on a body, the carriage attached to a proximal end of the connector and attached to an actuator; and controlling the actuator and connector to apply X-ray radiation across the length of the treatment area by moving the X-ray emitter.

38. The method of claim 37, the actuator being automatically controlled to move the carriage.

39. The method of claim 37, the actuator being manually controlled to move the carriage.

40. The method of claim 37, the controlling step further comprising automatically applying a voltage to the connector to cause the X-ray emitter to administer X-ray radiation to the treatment area.

41. The method of claim 37, further comprising the step of inputting values for a voltage, a dose, an increment length, and an overall lesion length to a control unit configured to automatically control the actuator and apply the voltage.

42. The method of claim 37, further comprising the step of positioning the X-ray emitter distal to the treatment area before the step of controlling the actuator.

43. A system for X-ray treatment in a passage within a body of a patient, the system comprising:

a sheath comprising a wall, a proximal end, and a distal end, the sheath wall defining a primary lumen longitudinally through the sheath;

a cable support tube, comprising a distal and a proximal end, the distal end of the support tube and a portion of the support tube being inside the sheath;

an X-ray emitter coupled to a cable, positionable within the cable support tube, and positionable within the primary lumen so that the X-ray emitter is near the distal end of the sheath;

means for allowing fluid flow around the X-ray emitter and permitting positioning of the X-ray emitter; and a cable pullback assembly comprising:
  a body;
  a carriage mounted on the body, the carriage slidable with respect to the body;
  a distal pullback adapter sealed onto a proximal end of the sheath, the distal pullback adapter being mounted on the body; and
  a proximal pullback adapter, sealed onto the cable, the proximal pullback adapter being mounted on the carriage.

44. The system of claim 43, in which the means for allowing fluid flow comprises a bellows comprising a collapsible tube having a first and a second end, where the first end of the bellows is connected to the proximal end of the sheath and the second end is connected to the proximal end of the cable support tube.

45. The system of claim 44, further comprising a fluid valve for inserting coolant fluid into the bellows and the catheter sheath.

46. The system of claim 43, in which the means for allowing fluid flow comprises a seal on the proximal end of the sheath for sealing between the catheter sheath and the cable support tube, the cable support tube being movable through the seal.

47. The system of claim 46, further comprising a fluid valve for inserting coolant fluid into the sheath.

48. A system for controlling an X-ray emitter to deliver X-ray radiation to a treatment area within a patient, the system comprising:

a pullback assembly comprising a body, a carriage slidably mounted on the body, a distal pullback adapter mounted on the body, and a proximal pullback adapter mounted on the carriage;

a catheter sheath sealed onto the distal pullback adapter, the catheter sheath having a proximal end and a distal end and defining a lumen extending longitudinally from the proximal end to the distal end;

an X-ray catheter sealed onto the proximal pullback adapter, the X-ray catheter having a distal end and a proximal end, the X-ray catheter comprising the X-ray emitter operatively coupled to a connector, the X-ray catheter positioned within the catheter sheath lumen; and a control unit, coupled to the connector and to the carriage, capable of applying voltage to the connector and comprising a power source, an actuator and a central processor.

49. The system of claim 48, further comprising an input device in the control unit, configured to input operation parameters.

50. The system of claim 49, further comprising a power source, operatively coupled to the X-ray emitter to apply a potential across an anode and a cathode within the X-ray emitter.

51. The system of claim 50, further comprising a calculation device, coupled to the input device and to the power source, configured to determine a dose increment of X-ray ray emitter operation and to activate the power source for the dose increment according to the operation parameters.

52. The system of claim 51, further comprising an actuator, mechanically coupled to the X-ray emitter and electronically coupled to the calculation device, configured to move the X-ray emitter past the treatment area according to operation parameters communicated by the calculation device.

53. The system of claim 51, further comprising a data storage device, coupled to the calculation device and configured to store actual operation parameters of the X-ray emitter during operation.

54. The system of claim 51, further comprising a display device, coupled to the calculation device and configured to display operation parameters and an operation status to an operator.

* * * * *